United States Patent [19]

Mead et al.

[11] Patent Number: 5,604,098
[45] Date of Patent: Feb. 18, 1997

[54] METHODS AND MATERIALS FOR RESTRICTION ENDONUCLEASE APPLICATIONS

[75] Inventors: David Mead; Neela Swaminathan, both of Madison, Wis.

[73] Assignee: Molecular Biology Resources, Inc., Milwaukee, Wis.

[21] Appl. No.: 362,741

[22] Filed: Dec. 22, 1994

Related U.S. Application Data

[63] Continuation of Ser. No. 36,481, Mar. 24, 1993, abandoned.

[51] Int. Cl.$^6$ .............................. C12Q 1/68; C12P 19/34; C07H 21/04; C12N 15/00
[52] U.S. Cl. .......................... 435/6; 435/91.1; 435/91.2; 435/172.1; 435/810; 536/23.1; 536/24.32; 536/24.33; 536/25.3; 536/25.32; 935/77; 935/78
[58] Field of Search ........................... 435/91.2, 172.3, 435/183, 810, 6; 536/24, 32, 23.1, 24.33, 25.3, 25.32; 436/94; 935/77, 78

[56] References Cited

U.S. PATENT DOCUMENTS 4,889,818  12/1989  Gelfand et al. ..................... 435/194

OTHER PUBLICATIONS

Burke, J. F. et al. Restriction fragment primed φX 174 single stranded DNA as template . . . Biochim. Biophys. Acta (1980) 609:205–223.
Xia, Y., et al. IL–3A virus infection of a Chlorella–like green alga induces a DNA restriction . . . Nucl. Acids Res. (1987) 15:6075–6090.
New England Biolabs 1990–1991 catalog, pp. 26 and 134.
Barany, F. The TaqI "star" reaction: strand preferences reveal hydrogen–bond donor and acceptor sites . . . Gene (1988) 65:149–165.
Anderson, Nucl. Acids Res. 9:3015–3027 (1981).
Baer, et al., Nature 310:207–211 (1984).
Bankier, et al., Methods in Enzymol. 155:51–93 (1987).
Burke et al., Science 236:800–812 (1987).
Deininger, Anal. Biochem 129:216–223 (1983).
Edwards, et al., Genomics 6:593–608 (1990).
Feinberg, et al., Anal. Biochem. 132:6–13 (1984).
Feinberg, et al., Anal. Biochem. 137:266–267 (1984).
Glenney, et al., J. Mol. Biol. 167:275–293 (1983).
Heininger, et al., Gene 1:291–303 (1977).
Kashles, et al., Proc. Natl. Acad. Sci. USA 85:9576–9571 (1988).
Komboj, et al., J. Cell Biol. 107:1835–1843 (1988).
Lion, et al., Anal. Biochem. 188:335–337 (1990).
Lo, et al., Nucleic Acids Res. 16:8719 (1988),
Lorenzo, et al., Eur. J. Biochem. 176:53–60 (1988).
Messing, Methods in Enzymol 101:20–78 (1983).
Roberts, et al., Nucl. Acids Res. 20:2167–2180 (1992).
Saiki, et al., Science 230:1350–1354 (1985).
Sanger, et al., Proc. Natl. Acad. Sci. USA 74:5463–5467 (1977).
Schriefer, et al., Nucl. Acids Res. 18:7455 (1990).

Primary Examiner—W. Gary Jones
Assistant Examiner—Bradley L. Sisson
Attorney, Agent, or Firm—Marshall, O'Toole, Gerstein, Murray & Borun

[57] ABSTRACT

The present invention is directed to materials and methods for the quasi-random and complete fragmentation of DNA using restriction endonuclease reagents capable of cutting DNA at a dinucleotide sequence. The invention is also directed to methods for labeling DNA using template-specific oligonucleotides, for shotgun cloning, for sequencing of DNA, for epitope mapping and for anonymous primer cloning, all using fragments of DNA generated by the method of the present invention.

29 Claims, 13 Drawing Sheets

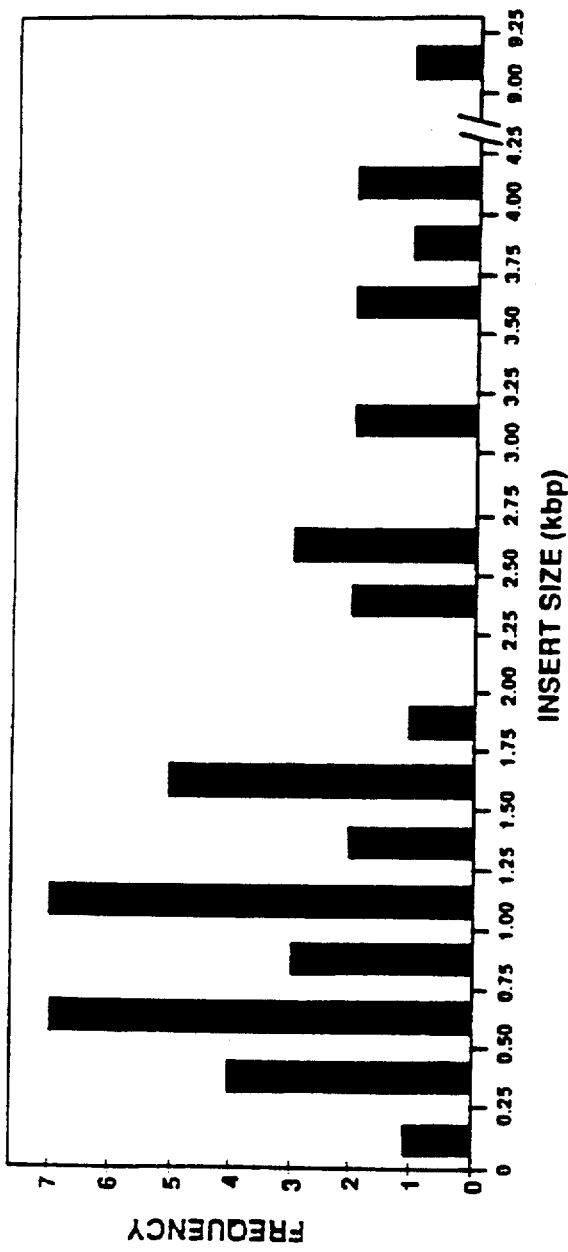
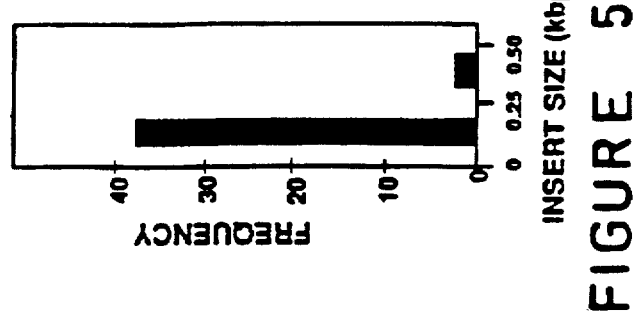
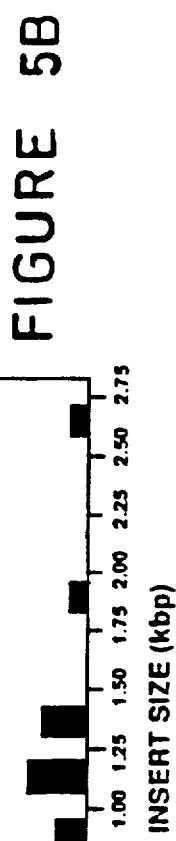
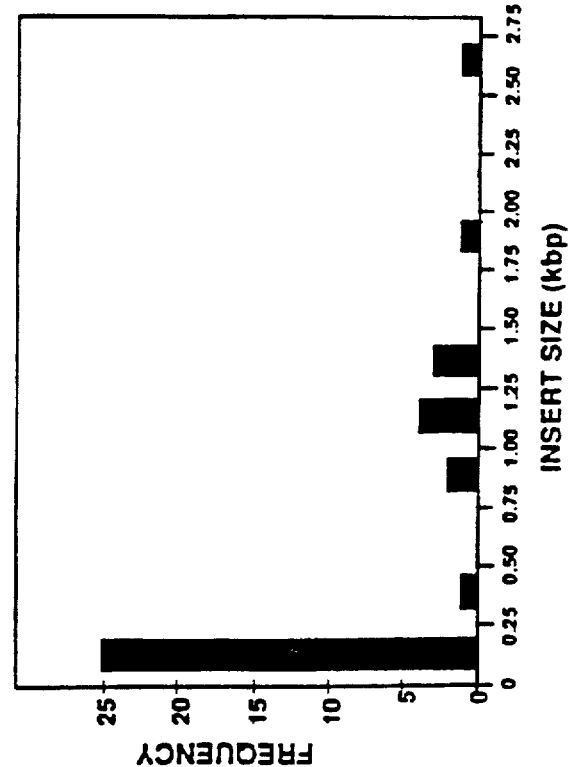
FIGURE 5A
FIGURE 5B
FIGURE 5C

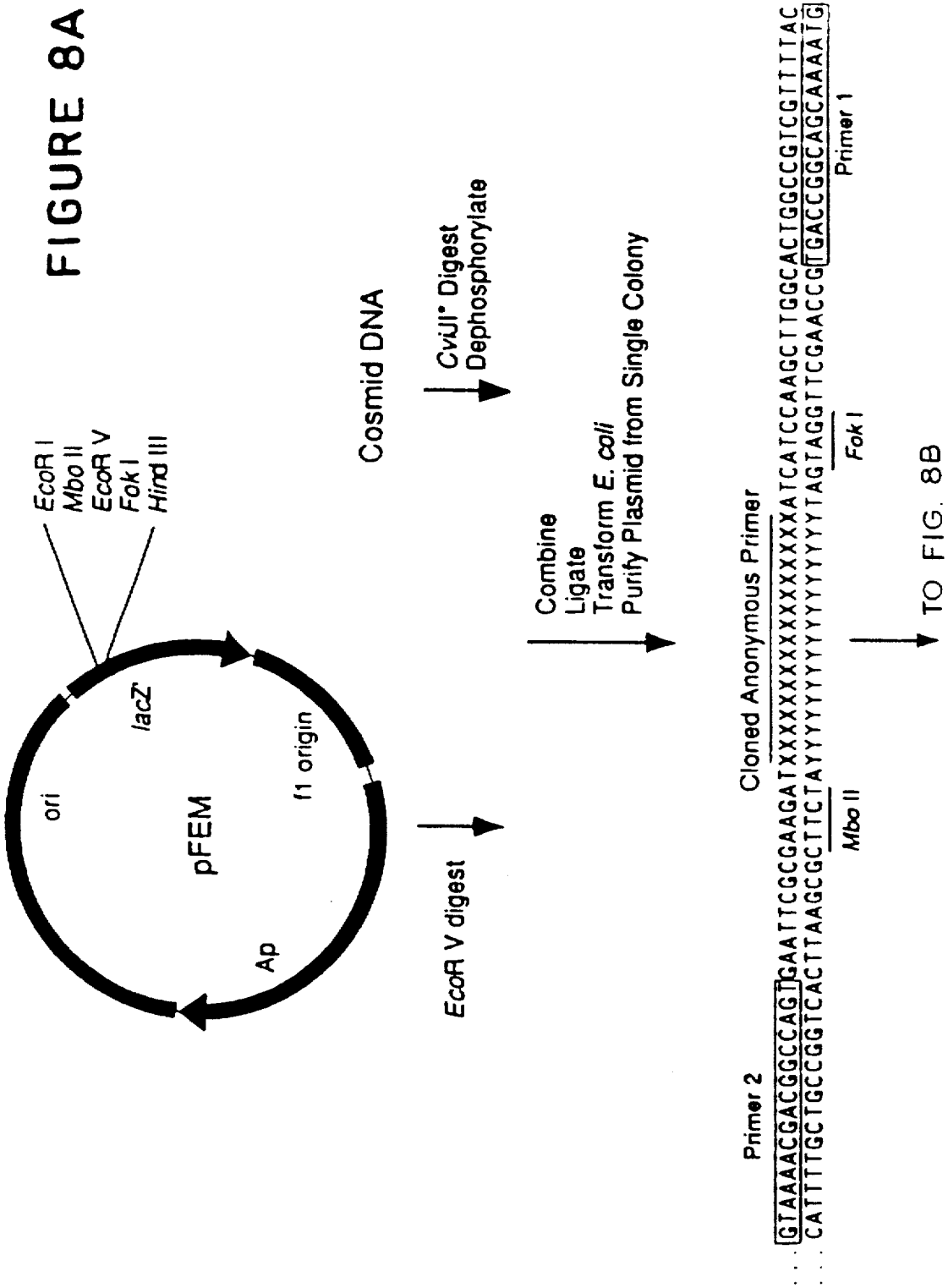

5,604,098

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

GTAAAACGAC GGCCAGT                                    17

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GCCAAGCTTG GATGAT                                    16

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ATCTTCGCGA ATTCACTGGC CGTCGTTTTA C            31

( 2 ) INFORMATION FOR SEQ ID NO:4:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GAATTCGCGA AGAT                                        14

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (x i) SEQUENCE DESCRIPTION: SEQ ID NO:5:

ATCATCCAAG CTTGGCACTG GCCGTCGTTT TAC    33

(2) INFORMATION FOR SEQ ID NO:6:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:6:

GTAAAACGAC GGCCAGTGAA TTCGCGAAGA TNNNNNNNNN NNNNNNNNAT CATCCAAGCT    60

TGGCACTGGC CGTCGTTTTA C    81

(2) INFORMATION FOR SEQ ID NO:7:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:7:

GTAAAACGAC GGCCAGTGCC AAGCTTGGAT GATNNNNNNN NNNNNNNNNN ATCTTCGCGA    60

ATTCACTGGC CGTCGTTTTA C    81

METHODS AND MATERIALS FOR RESTRICTION ENDONUCLEASE APPLICATIONS

This is a continuation of U.S. application Ser. No. 08/036,481, filed Mar. 24, 1993, now abandoned.

FIELD OF THE INVENTION

This invention relates to methods for partially or completely digesting DNA at a dinucleotide sequence. More particularly, this invention relates to methods of generating quasi-random fragments of DNA, and methods of cloning, labeling, and sequencing DNA, as well as epitope mapping of proteins. This invention also relates to methods for generating sequence-specific oligonucleotides from DNA, without prior knowledge of the nucleic acid sequence of such DNA, and to methods for cloning and labeling DNA after restriction digestion by a two base recognition endonuclease reagent. This invention also relates to methods for cloning, labeling, and detecting nucleic acids using two base restriction endonuclease reagents, such as CviJ I, BsuR I, or CGase I.

BACKGROUND OF THE INVENTION

Restriction endonucleases are invaluable tools in modern molecular biology. These molecular scissors have numerous uses in areas including molecular cloning, restriction mapping, deletion mutagenesis, and others.

Restriction enzymes bind specifically to and cleave double-stranded DNA at specific sites within or adjacent to a particular sequence known as the recognition sequence. These enzymes have been classified into three groups. Because of the properties of the type I and type III enzymes, they have not been widely used in molecular biology applications, and will not be discussed further. Type II enzymes are part of a binary system known as a restriction modification system consisting of a restriction endonuclease that cleaves a specific sequence of nucleotides and a separate DNA modifying enzyme that modifies the same recognition sequence and thereby prevents cleavage by the cognate endonuclease. A total of about 2103 restriction enzymes are known, encompassing 179 different type II specificities (Roberts, et al., *Nucl. Acids Res.* 20:2167–2180 (1992)). Although there are more than 1200 type II restriction enzymes, many of them are members of groups which recognize the same sequence. Restriction enzymes which recognize the same sequence are said to be isoschizomers.

The vast majority of type II restriction enzymes recognize specific sequences which are four, five, or six nucleotides in length and which display twofold (palindromic) symmetry. A few enzymes recognize longer sequences or degenerate sequences.

The location of cleavage sites within a palindrome differs from enzyme to enzyme. Some enzymes cleave both strands exactly at the axis of symmetry generating fragments of DNA that carry blunt ends, while others cleave each strand at similar sequences on opposite sides of the axis of symmetry, creating fragments of DNA that carry protruding, single-stranded termini.

Restriction endonucleases with shorter recognition sequences cut DNA more frequently than those with longer recognition sequences. For example, assuming a 50% G-C content, a restriction endonuclease with a 4-base recognition sequence will cleave, on average, every $4^4$ (256) bases compared to every $4^6$ (4096) bases for a restriction endonuclease with a 6-base recognition sequence. Under certain conditions some restriction endonucleases are capable of cleaving sequences which are similar but not identical to their defined recognition sequence. This altered specificity has been termed "star" (*) activity and is observed only under certain nonstandard reaction conditions. The manner in which an enzyme's specificity is altered depends on the particular enzyme and on the conditions employed to induce the star activity. Conditions that contribute to star activity include high glycerol concentration, high ratio of enzyme to DNA, low ionic strength, high pH, the presence of organic solvents, and the substitution of $Mg^{++}$ with other divalent cations. The most common types of star activity involve cutting at a recognition sequence having a single base substitution, cutting at sites having truncation of the outer bases of the recognition sequence, and single-strand nicking. The following restriction endonucleases show star activity: Ase I, BamH I, BssH II, BsuR I, CviJ I, EcoR I, EcoR V, Hind III, Hinf I, Kpn I, Pst I, Pvu II, Sal I, Sca I, Taq I, and Xmn I. Star activity is generally viewed as undesirable, and of little intrinsic value.

Of the 179 unique type II restriction endonucleases, 31 have a 4-base recognition sequence, 11 have a 5-base recognition sequence, 127 have a 6-base recognition sequence, and 10 have recognition sequences of greater than 6 bases. In two cases, a restriction endonuclease has a recognition sequence of less than 4 bases.

The restriction enzyme CviJ I has a three base recognition sequence or a two-base recognition sequence, depending on the reaction conditions. Under normal reaction conditions CviJ I recognizes the sequence PuGCPy (wherein Pu=purine and Py=pyrimidine) and cleaves between the G and C to leave blunt ends (Xia et al., 1987. *Nucleic Acids Res.* 15:6075–6090). Under "relaxed" or "star" conditions (in the presence of 1 mM ATP and 20 mM DTT) the specificity of CviJ I may be altered to cleave DNA more frequently. This activity is referred to as CviJ I*, for star or altered specificity. However, CviJ I* activity is not observed under conditions which favor star activity of other restriction endonucleases.

The restriction enzyme BsuR I normally recognizes the sequence GGCC and cleaves between the G and C to leave blunt ends. (Heininger, et al., *Gene* 1:291–303 (1977)). Under relaxed conditions (high pH, low ionic strength, and high glycerol concentration) the specificity of Bsu RI may be altered to cleave DNA more frequently. An isoschizomer of this enzyme, Hae III, does not display this star activity.

Among the most important techniques in molecular biology are the techniques which permit the labeling of DNA or RNA with radioactive or non-radioactive labels. The most commonly used methods of labeling double-stranded DNA are the nick translation method, (Maniatis, et al., *Molecular Cloning: A Laboratory Manual*, Cold Spring Harbor Laboratory Press, Cold Spring Harbor, N.Y. (1982)), and the random primer labeling (RPL) method (Feinberg, et al., *Anal. Biochem.* 132:6–13 (1984); Feinberg, et al., *Anal. Biochem.* 137:266–267 (1984)).

The nick translation method involves nicking of template DNA under carefully controlled conditions using DNAse I. DNA polymerase I is then added to the nicked DNA to facilitate the addition of nucleotides at the 3' end and removal of nucleotides at the 5' end of a nick. This process replaces pre-existing nucleotides with labeled nucleotides. The main disadvantage of this labeling system is the sensitive balance required between the concentrations of the nicking enzyme DNAse I and the synthesis enzyme DNA polymerase I; too little or too much of either enzyme significantly reduces the efficiency of the incorporation.

In the RPL method, synthetic oligonucleotide primers six to nine bases long (synthesized in all possible base combinations) are hybridized to denatured DNA. The hybridized primers serve to prime DNA synthesis by either the Klenow fragment of DNA polymerase I, T7 DNA polymerase, or other suitable DNA polymerases. Although typically yielding probes of relatively high specific activity, there are several disadvantages associated with RPL: the primers synthesized are random in sequence and are not specific for the template, hence large quantities of primer are needed for adequate template hybridization; the primers are 6 to 9 nucleotides long, which limits the temperature at which synthesis can occur and therefore the choice of the enzymes that may be used; and most RPL protocols use the Klenow fragment of DNA polymerase I, which is not a highly processive enzyme and therefore requires long incubation times in order to achieve maximum incorporation.

RPL typically yields probes having higher specific activity than probes produced by nick translation, and, thus, RPL has become a preferred method for labeling DNA. For example, the nick translation method routinely yields probes having specific activities of about $10^8$ cpm/μg DNA while the RPL routinely yields specific activities of about $10^9$ cpm/μg DNA.

Oligonucleotides are essential tools in many molecular biology applications, including sequencing, labeling and hybridization for detection, polymerase chain reaction (PCR) and other forms of nucleic acid amplification, mutagenesis, nucleic acid capture and enrichment, and cloning. The development of methods for controlling the chemical synthesis of oligonucleotides 2–200 bases in length has accelerated the evolution of modern molecular genetics.

The use of synthetic oligonucleotides for labeling and detection is an important tool in research and clinical labs. Conventional methods for labeling synthetic oligonucleotides generally employ one oligonucleotide containing one or a few labels. There are several methods for labeling oligonucleotides at the 5' or 3' ends using $^{32}$P-dNTP (dNTP= deoxynucleoside triphosphate), biotin-11-dUTP, fluorescein-dUTP, DNP-dNTP (DNP=dinitrophenol), digioxigenin-dUTP etc. as labels. One method, 5' end labeling, is achieved by a forward or exchange reaction using polynucleotide kinase. In the forward reaction $\gamma^{32}$P from $[\gamma^{32}$P] -ATP is added to a dephosphorylated 5' end of the oligonucleotide and in the exchange reaction an excess of ADP is used to cause an exchange of the terminal 5' phosphate from DNA to ADP followed by transfer of the $\gamma^{32}$P from $\gamma^{32}$P-ATP to the 5' end of the DNA. Homopolymeric tailing is another method for labeling oligonucleotides and involves addition of polynucleotides at the 3' end of the oligonucleotide using labeled nucleotides in the presence of a divalent cation and terminal deoxynucleotidyl transferase. The use and disposal of hazardous radioisotopes for all three methods is a significant disadvantage in research and clinical settings. The use of non-radioactive labels is a safer alternative to isotopes, and in general the level of detection is sensitive enough for some applications. However, there are numerous applications which are limited by the detection sensitivity of singly-labeled oligonucleotides.

The polymerase chain reaction is an exponential DNA amplification procedure based on repeated cycles of denaturation, oligonucleotide primer annealing, and primer extension by a thermostable DNA polymerase, such as the enzyme isolated from *Thermus aquaticus* (Saiki et al.,

*Science* 230:1350–1354 (1985)). The nucleotide sequence of the ends of the DNA must be known in order to synthesize the two oligonucleotides required for this amplification method. PCR has also been used to generate homogeneously-labeled probes using modified deoxynucleotide triphosphates such as digoxigenin-11-dUTP or biotin-11-dUTP (Lion et al., *Anal. Biochem.* 188:355–337 (1990); Lo et al., *Nucleic Acids Res.* 16:8719 (1988)).

Epitope mapping is another important technique in molecular biology. Epitope mapping is the precise identification of an epitope associated with a function or structure within a protein. Hence, a binding domain of a protein may be determined using an array of approaches.

One method of epitope mapping involves the digestion of a pure protein into smaller fragments using specific proteases for different time periods, separation of the fragments on SDS-PAGE (ordering the fragments), transfer onto membrane, binding to antibodies or radioactive ligands, and isolation of the smallest peptide either by affinity chromatography or extraction from gels or membrane for peptide sequencing (Glenney et al., *J. Mol. Biol.* 167:275–293 (1983)).

Another epitope mapping method involves cloning cDNA encoding the protein of interest into an expression vector. The cloned cDNA is truncated using a restriction endonuclease or Bal 31 nuclease for subsequent expression in an appropriate vector. A truncated protein may then be expressed in vitro by a cellular transcription and translation system followed by immunoprecipitation with an antibody or ligand to identify the smallest protein which binds to it. By identification of a segment of the cDNA corresponding to the expression of that protein, a clone is isolated and sequenced to yield information as to the epitope of interest (Lorenzo et al., *Eur. J. Biochem.* 176:53–60 (1988)).

Site-directed mutagenesis may also be used in epitope mapping. In this method, oligonucleotides are utilized to generate site specific alterations in cDNA encoding a protein of interest, and the mutant cDNA is introduced into cells which lack the protein. The cells may then express the altered protein which may be assayed for function, e.g., ligand binding (Kashles et al. *Proc. Natl. Acad. Sci. U.S.A.* 85:9576-9571 (1988)).

Epitope mapping may also be performed by restriction digestion of DNA into multiple fragments followed by insertion into an expression vector for the expression and analysis of the function of the resulting protein. (Kamboj, et al. *J. Cell Biol.* 107:1835–1843 (1988)).

However, each of these methods has limitations and most of these methods require detection of a loss of function. A superior approach is to test for the presence of a function.

A limitation of the first approach to epitope mapping described above is that the protein must be purified to homogeneity and available in large amounts in order to isolate peptides which may be sequenced. This is a major problem because many functionally important proteins are present in low quantities, and the purification of these proteins to homogeneity requires several steps which may not ensure a desired quantity or purity of the protein. Even if the protein is pure, the peptides must be run on special gels to ensure that the ends of the peptides are not blocked for sequencing. Many labs have spent up to a year purifying such proteins and have failed to obtain a sequence, either due to contaminants or the end-blockage of the peptides.

The second approach involves deletions from the C-terminus followed by subcloning of DNA encoding proteins having these deletions in order to express them. A number of clones are picked and assayed separately for the presence or absence of the epitope. This is followed by identification of the extent of a deletion by comparison to the known sequence. This approach is tedious and requires careful control of Bal 31 digestion of the DNA.

In situations where restriction fragments are used for epitope mapping, each fragment is subcloned. This approach requires numerous manipulations to generate inframe start and stop codons for each fragment. Identification of precise domains may require yet another approach, such as synthesis and subcloning of oligonucleotides or site-directed mutagenesis of a target region.

Site-directed mutagenesis requires prior knowledge of the region to be targeted. This approach involves subcloning and sequencing of several subclones to ensure that the mutation has been introduced, and involves analyses of loss of function.

The cloning and sequencing of DNA is crucial to the understanding of genome organization and to nearly every other endeavor undertaken in molecular biology and molecular genetics. Clone banks of DNA are important to the nucleotide sequence analysis of organisms and their genes. Depending on the circumstances, a library of clones may be enriched for or unbiased against the particular genetic unit under analysis. A variety of biochemical and biophysical strategies have been utilized to construct such libraries (Sambrook et al. *Molecular Cloning: A Laboratory Manual*, Second edition. Cold Spring Harbor Laboratory Press; Cold Spring Harbor N.Y. (1989)). Most large scale DNA sequencing strategies depend on randomly fragmenting a target molecule into small pieces which may be subcloned into a bacteriophage such as M13 (Messing, *Methods in Enzymol* 101:20–78 (1983); Baer et al., *Nature*, 310:207–211 (1984); Bankier et al., *Methods in Enzymol* 155:51–93 (1987); Edwards et at., *Genomics* 6:593–608 (1990); Davison, *J. DNA Seq. and Mapping* 1:389–394 (1991)). These vectors produce template DNA in a single-stranded form, the optimal substrate for enzymatic sequence analysis (Sanger et al., *Proc. Natl. Acad. Sci. U.S.A.* 74:5463–5467 (1977)). The data obtained from such cloned subfragments are combined and overlapped until approximately 80–95% of both strands are covered; after which gap filling techniques are typically utilized to complete the sequence.

Four methods are generally used to fragment large DNAs into a size suitable for enzymatic sequence analysis: DNAse I treatment (Anderson, *Nucl. Acids Res.* 9:3015–3027 (1981)); low pressure shearing (Schriefer et al., *Nucl. Acids Res.* 18:7455 (1990)); sonication (Deininger, *Anal Biochem* 129:216–233 (1983)), and digestion with restriction enzymes. Sonication, low pressure shearing, and treatment with DNAse I all break DNA randomly and result in a collection of overlapping fragments. In addition, sonication and low pressure shearing tend to shear the middle of the targets, so that a preliminary pre-ligation is necessary to equalize the representation of the DNA ends in the final library. Another drawback to these methods is the inefficiency with which the resultant jagged ends may be ligated, necessitating an enzymatic end-repair step prior to cloning. Sonication, the most commonly used method, requires relatively large amounts of DNA, results in a low transformation efficiency and is technically difficult to automate. DNAse I requires recalibration with new batches and age, is sensitive to trace contaminants, and is somewhat variable in its digestion rate. Although fragmentation with restriction enzymes is attractive due to the relative abundance of sequence specificities available, a complete restriction digest results in non-overlapping fragments and partial digests often exhibit non-uniform restriction rates. Generally, as many as four separate libraries utilizing four different restriction digests must be prepared to supply overlaps between fragments.

The steps involved in constructing a random clone library (shotgun cloning) for DNA sequencing by current methods include: 1) isolating the DNA fragment, 2) ligating the DNA to itself, 3) randomly shearing the material by sonication, 4) repairing the ragged ends with a DNA polymerase or nuclease, 5) size fractionation by preparative agarose gel electrophoresis, 6) extraction with organic chemicals to re-purify the DNA, 7) ligating the product into a bacteriophage cloning vector, usually M13mp18 or 19, and 8) transforming special strains of competent *E. coli*, (Bankier et al., *Methods in Enzymol.* 155:51–93 (1987)). These steps are inherently difficult to automate and require large amounts of DNA, because the sonication and/or fractionation steps result in low cloning efficiencies. In addition, the entire process is lengthy, typically requiring several days for a skilled researcher to complete.

SUMMARY OF THE INVENTION

The present invention is directed to a method for the digestion of DNA with a restriction endonuclease reagent under conditions wherein said DNA is cleaved at a dinucleotide sequence selected from the group consisting of PyGCPy, PuGCPy, PuGCPu, and wherein Pu=purine and Py=pyrimidine.

The present invention is also directed to a method for restriction endonuclease digestion of DNA comprising the step of digesting DNA with a restriction endonuclease reagent under conditions wherein said DNA is digested at 11 of 16 possible dinucleotide sequences and wherein said dinucleotide sequences are selected from the group consisting of PuCGPu, PuCGPy, PyCGPy, and PyCGPu, and wherein Pu=purine and Py=pyrimidine.

The present invention is directed to shotgun cloning of DNA, epitope mapping, and for labeling DNA using the digestion methods of the present invention. The present invention provides methods for the quasi-random fragmenting of DNA using the digestion methods of the present invention under conditions wherein the DNA is only partially cleaved and the site preference of the restriction endonuclease reagent is greatly reduced. By quasi-random is meant an overlapping population of DNA fragments produced by digesting DNA using the methods of the present inventions without apparent site-preference and which appears as a smear upon electrophoresis in a 1–2 wt. % agarose gel. The present invention is also directed to the shotgun cloning and sequencing of quasi-random fragments of DNA produced by the methods of the present invention. Quasi-random fragments in the shotgun cloning method of the present invention are produced by partial digestion of DNA with a restriction endonuclease reagent according to the methods of the present invention. More particularly, quasi-random fragments of DNA useful in the cloning method of the present invention are produced by the partial digestion of the DNA to be cloned with CviJ I, BsuR I or with a restriction endonuclease reagent termed CGase I comprising Taq I and Hpa II. Quasi-random fragments having a length of between about 100 and about 10,000 nucleotides are preferred. More preferred are quasi-random fragments of about 500 to about 10,000 nucleotides in length. The present invention is also directed to the generation of quasi-random fragmentation of DNA using the method of the present invention for the purposes of epitope mapping and gene cloning. These quasi-random fragments are expressed either in vitro or in vivo and the smallest fragment containing the desired function is identified by screening assays well known in the art.

The present invention is also directed to the production of anonymous primers from any DNA without prior knowledge of the nucleotide sequence. The present invention provides methods for anonymous primer cloning and sequencing after the complete digestion of DNA utilizing CviJ 1, BsuR 1 or CGase I using the methods of the present invention.

Additionally, the present invention is directed to methods of labeling and detecting DNA comprising the complete digestion of DNA using the methods of the present invention, followed by a heat denaturation step, to yield sequence specific oligonucleotides. In particular, an aspect of the present invention involves labeling DNA with sequence specific oligonucleotides of about 20 to about 200 bases in length (with an average size of between 20–60 bases) generated by CviJ I, BsuR I or CGase I digestion of the template DNA.

More particularly, the invention is directed to restriction generated oligonucleotide labeling (RGOL) of DNA which comprises the digestion of an aliquot of template DNA with CviJ I followed by a simple heat denaturation step, thereby generating numerous sequence specific oligonucleotides, which can then be utilized for labeling nucleic acids by a number of methods, including primer extension type reactions with a DNA polymerase and various labels, isotopic or non-isotopic (RGOL-PEL); 5' end labeling with polynucleotide kinase; 3' end labeling using terminal transferase and various labels, isotopic or non-isotopic. Labeling at the 3' end, also referred to as tailing, adds numerous labels per oligonucleotide (1–200), depending on the labeling conditions. The addition of 10–100 labels per oligonucleotide, in conjunction with the 100–500 oligonucleotides generated per template, results in a significant signal amplification not obtainable by conventional methods.

The invention is also directed to thermal cycle labeling (TCL) which comprises the simultaneous labeling and amplification of probes utilizing CviJ I or CGase I restriction generated oligonucleotides as the starting material. In this method, natural DNA of unknown sequence is digested with CviJ I to generate numerous double-stranded fragments which are then heat denatured to yield oligonucleotides. These oligonucleotides are combined with the intact template and subjected to repeated cycles of denaturation, annealing, and extension in the presence of a thermal stable polymerase, deoxynucleotide triphosphates and the appropriate buffer. Alpha $^{32}$P-dATP (or any of the other three deoxynucleotide triphosphates), biotin-dUTP, fluorescein-dUTP, or digoxigenin-dUTP is incorporated during the extension step for subsequent detection purposes. Thermal cycle labeling efficiently labels DNA while simultaneously amplifying large amounts of the labeled probe. In addition, TCL probes exhibit a 10 fold improvement in detection sensitivity compared to conventional probes. Isotopic labels useful in the nature of the present invention include but are not limited to $^{32}$P, $^{33}$P, $^{35}$S, $^{14}$C and $^{3}$H. Non-isotopic labels useful in the present invention include but are not limited to fluorescein, biotin, dinitrophenol and digoxigenin.

The present invention is also directed to an improved method for purifying CviJ 1 from the algae Chlorella infected with the virus IL-3A.

In addition, the present invention is directed to restriction endonuclease reagents which, under conditions which relax the sequence specificity of one or more restriction endonucleases, cleave DNA at the dinucleotide sequences AT or TA.

The present invention is also directed to a restriction endonuclease reagent comprising in combination, Taq I and Hpa II, which is capable of digesting DNA at 11 of 16 possible dinucleotide sequences, said sequences selected from the group consisting of PuCGPu, PuCGPy, PyCGPy and PyCGPu, and wherein Pu=purine and Py=pyrimidine.

The following examples are intended to be illustrative of the several aspects of the present invention and are not intended in any way to limit the scope of any aspect of the present invention.

BRIEF DESCRIPTION OF THE DRAWINGS

FIG. 5A. Size distribution of DNA fragments produced by partial digestion of DNA by CviJ I and fractionated by micro-column chromatography.

FIGS 5B–5C size distributions of DNA fragments produced by partial digestion of a DNA by CviJ I and fractionated by agarose gel electrophoresis.

FIGS. 8A–8B are in combination a flow chart depicting an "Anonymous Primer Cloning Strategy".

DETAILED DESCRIPTION OF THE INVENTION

Figure 1A:
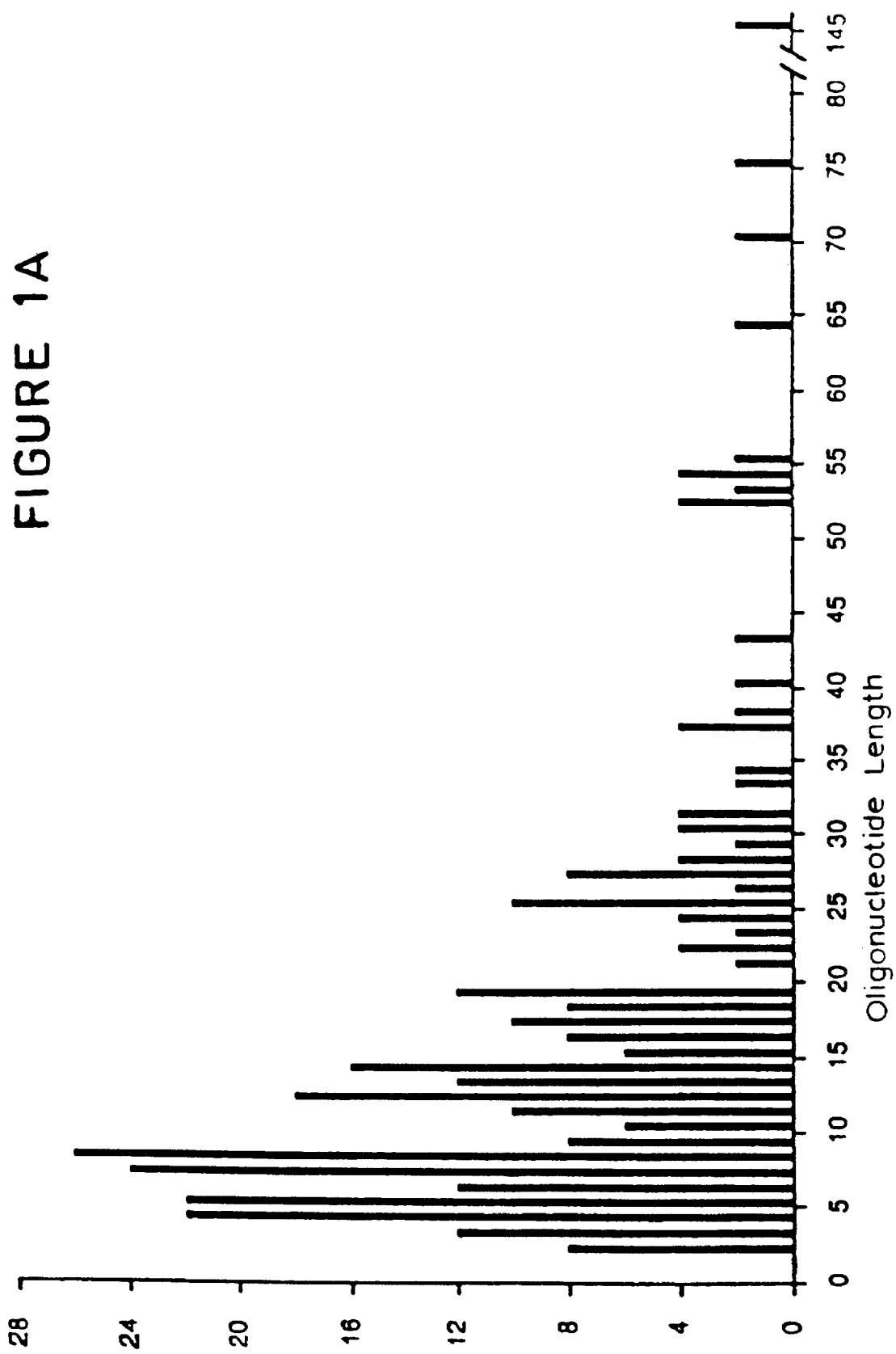
FIG. 1A is a graphic representation of the theoretical frequency and distribution of oligonucleotides which should be generated by CviJ I* digestion of pUC19.

The present invention is directed to a method for the fragmentation and cloning of DNA using the restriction endonuclease CviJ I under conditions which allow the enzyme to cleave DNA at the dinucleotide sequence GC. The present invention is also directed to the cloning of quasi-random fragments of DNA digested using the fragmentation method of the present invention.

As an alternative to the methods for constructing random clone libraries described above, methods were devised for the construction of such libraries which require fewer steps and reagents, which require smaller amounts of DNA, which have relatively high cloning efficiencies and which takes less time to complete. These methods relate to the recognition that a partial digest with a two or three base recognition endonuclease cleaves DNA frequently enough to be functionally random with respect to the rate at which sequence data may be accumulated from a shotgun clone bank. The restriction enzyme CviJ I normally recognizes the sequence PuGCPy and cleaves between the G and C to leave blunt ends (Xia et al., *Nucl. Acids Res.* 15:6075–6090 (1987)). Under "relaxed" conditions (in the presence of 1 mM ATP and 20 mM DTT) the specificity of CviJ I can be altered to cleave DNA more frequently and perhaps as frequently as at every GC. This activity is referred to as CviJ I*. Because of the high frequency of the dinucleotide GC in all DNA (16 bp average fragment size for random DNA), quasi-random libraries may be constructed by partial digestion of DNA with CviJ I*. A DNA degradation method with low levels of sequence specificity produces a smear of the target DNA when analyzed by agarose gel electrophoresis. Digestion of the plasmid pUC19 under partial CviJ I* conditions does not result in a non-discrete smear; rather, a number of discrete bands are found superimposed upon a light background of smearing, suggesting that CviJ I* has some site preference. Atypical reaction conditions according to the present invention reduce this apparent site preference of CviJ I* to produce an activity (termed CviJ I) which results in a quasi-random distribution of DNA fragments. The use of the restriction enzyme CviJ I, in combination with a rapid gel filtration size exclusion step, streamlines a number of aspects involved in shotgun cloning.

One aspect of the present invention involves the use of the two/three base recognition endonuclease CviJ I, in conjunction with a simple spin-column method to produce libraries equivalent in final form to those generated by the combination of sonication and agarose gel electroelution. However, the method of the present invention requires fewer steps, a shorter time period, and significantly less substrate (nanogram amounts) when compared to conventional procedures. Both small and large sequencing projects using the methods described herein are within the scope of the present invention.

Current sequencing paradigms require the generation of a new template for each 350–500 nucleotides sequenced. On this basis, sequencing both strands of the human genome would require at least 12 million templates 500 nucleotides long, assuming no overlap between templates.

A random approach, such as shotgun sequencing, would require 30 to 50 million templates, assuming the entire genome were randomly subcloned. As many as 250,000 libraries may be needed to generate the requisite templates from a subcloned and ordered array of this genome, depending on the type of vector utilized, and the degree of overlap between such clones. The ability to generate shotgun libraries in a semi-automated, microtiter plate format would greatly simplify such large scale projects.

The development of methods for cloning large DNA molecules in yeast artificial chromosomes (Burke et al., *Science* 236:806–812 (1987)), or in bacteriophage P1-derived vectors (Steinberg, *Proc. Natl. Acad. Sci. U.S.A.* 87:103–107 (1990)), simplifies the subdivision and analysis of very large genomes. However, the large size of the resulting subclones (100–1000 kbp) presents additional challenges for subsequent sequencing efforts. A report of the sequencing of a 134 kbp genome by random shotgun cloning directly into a bacteriophage M13 vector indicates that numerous intermediate stages of subcloning, mapping, and overlapping such clones may be eliminated (Davison, *J. DNA Seq. and Mapping* 1:389–394 (1992)). An order of magnitude reduction in the amount of DNA required for shotgun cloning would substantially simplify efforts to directly sequence 100,000 bp sized molecules and beyond.

The ability to generate an overlapping population of randomly fragmented DNA molecules is considered essential for minimizing the closure of nucleotide sequence gaps by the shotgun cloning method. The use of a very frequent-cutting restriction enzyme, such as CviJ I, is an approach which has not been utilized. Reaction conditions according to the present invention result in the quasi-random restriction of pUC19 and lambda DNA, as judged by the degree of smearing observed.

The randomness of this CviJ I reaction was quantified by sequence analysis of 76 such partially-fragmented pUC19 subclones. The analysis showed that CviJ I partial digestion (limiting enzyme and time) restricts DNA at PyGCPy, PuGCPu, and PuGCPy (but not PyGCPu), and is thus a hybrid reaction which combines the three base recognition specifity of CviJ I with the "two" base recognition specifity of CviJ I*. Interestingly, most of the "relaxed" cleavage observed under CviJ I conditions occurred in those portions of the sequence which were deficient in "normal" restriction sites. CviJ I treatment produces a relatively uniform size distribution of DNA fragments, permitting sequence information to be accumulated in a statistically random fashion.

Figure 2:
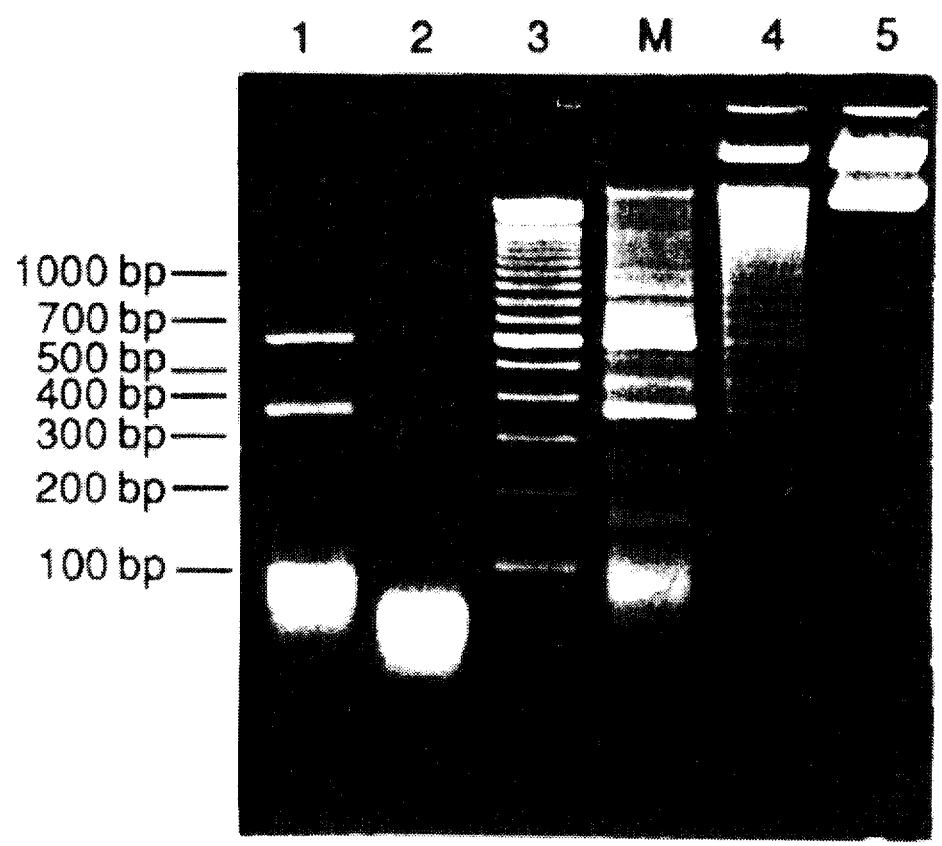
FIG. 2 is a photographic reproduction of a gel depicting complete digestion of pUC19 DNA with CviJ I, complete digestion of pUC19 DNA with CviJ I*, partial digestion of pUC19 DNA with CviJ I*, partial digestion of pUC19 with CviJ I**, and uncut pUC19.

Shotgun cloning with CviJ I digested DNA is efficient partly because the resulting fragments are blunt ended. Other methods currently used to randomly-fragment DNA, including sonication, DNAse I treatment, and low pressure shearing, leave ragged ends which must be converted to blunt ends for efficient vector ligation. Other than a heat denaturation step to inactivate the endonuclease, no additional treatments are required for cloning CviJ I restricted DNA. In addition, the preligation step required to equalize representation of the ends of a DNA molecule prior to sonication or DNAse I treatment is not necessary with CviJ I** fragmentation. CviJ I* cleaves its cognate recognition site very close to the ends of a linear molecule, as judged by the very small fragments resulting from complete digestion of pUC19 as depicted in FIG. 2, lane 1.

The overall efficiency of shotgun cloning depends not only on the fragmentation process, but also upon the size fractionation procedure used to remove small DNA fragments. The efficiency of cloning agarose gel fractionated DNA was found to be unexpectedly variable. Numerous experiments produced an erratic distribution of sized material and the resulting-cloned inserts were uniformly small (70%<500 bp in one trial, 100%<500 bp in another). The method of the present invention includes a simple and rapid micro-column fractionation method, which has resulted in three to thirteen times more transformants than agarose gel fractionation. More importantly, the size distribution of the cloned inserts from column-fractionated DNA was skewed toward larger fragments (88%>500 bp). Micro-column fractionation also eliminates the chemical extraction steps required for agarose fractionated DNA. After the target DNA has been column-fractionated, no further treatments are required for cloning. Combining CviJ I** partial restriction with micro-column fractionation permits the construction of useful libraries frown as little as 200 ng of substrate, an order of magnitude less starting material than recommended for sonication/end-repair and agarose gel fractionation procedures.

The CviJ I** reaction represents a unique alternative for controlling the partial digestion of DNA, a technique which is fundamental to the construction of genomic libraries (Maniatis et al., *Cell* 15:687–701 (1978)), and restriction site mapping of recombinant clones (Smith, et al., *Nucl. Acids Res.* 3:2387–2398 (1976)). Partial DNA digests are notably variable and are strongly dependent on the concentration and purity of the DNA, the amount of enzyme used, the incubation time, and the batch of enzyme. Partial digestions may also be variable with respect to the rate at which a particular recognition sequence is cleaved throughout the substrate. Optional reaction conditions, such as those which render such partial digests independent of one or more of these variables, allows more precise control of the end product. Several controlling schemes may be employed, including: the addition of a constant amount of carrier DNA (Kohara et al., Cell 50:495–508 (1987)), the use of limiting amounts of $Mg^{2+}$ (Albertson et al. Nucl. Acids Res. 17:808 (1989)), ultraviolet irradiation (Whitaker, et al., Gene 41:129–134), and the combination of a restriction enzyme and a sequence complementary DNA methylase (Hoheisel et al., Nucl. Acids Res. 17:9571–9582 (1989)). Utilizing three different batches of CviJ I, and three different DNA templates from five separate preparations, a uniform CviJ I** partial digestion pattern was obtained that was primarily time-dependent when a constant ratio of 0.3 units of enzyme per µg of DNA was used.

The rate at which a particular restriction site is cleaved at different locations in a substrate is variable for many endonncleases (Brooks, et al., Methods in Enzymol., 152:113–129 (1987)). Reaction conditions for CviJ I may be optimized to substantially reduce the site preferences of this enzyme during partial digestion (see FIG. 2, lanes 3 and 4). Normally, "star" reaction conditions result in cleavage at new sites. The use of star reaction conditions according to the present invention (dimethyl sulfoxide (DMSO) and lowered ionic strength) to affect the partial digestion activity of CviJ I* does not result in an altered restriction site cleavage as assayed by sequencing the products of 76 digestion reactions. Instead, the relative rate of cleavage of individual sites appears to be more uniform under these conditions. A 3–5 fold increase in the rate of normal CviJ I restriction with the standard buffer and DMSO, further substantiates this approach. All of these results indicate that, under the appropriate reaction conditions, CviJ I is useful for a number of other applications, such as high resolution restriction mapping and fingerprinting, diagnostic restriction of small PCR fragments, and construction of genomic DNA libraries.

Another aspect of the present invention involves quasi-random fragmentation of DNA using the method of the present invention for epitope mapping and cloning intact genes. The same method as described above for shotgun cloning is utilized, except that an expression vector is used to generate functional proteins from the DNA.

Another aspect of the present invention involves fragmenting DNA using the present invention to generate multiple oligonucleotides from any double-stranded DNA template. Restriction-generated oligonucleotides (RGO) are sequence specific oligonucleotides generated from any DNA according to the present invention. CviJ I* presumably cleaves the recognition sequence GC between the G and C to leave blunt ends (Xia et al., Nucl. Acids Res. 15:6075–6090, (1987)). Because of the high frequency of the dinucleotide GC in all DNA (16 bp average fragment size for random DNA), a complete CviJ I* restriction results in numerous fragments which are about 20–200 bp in size. These restriction fragments are generated from an aliquot of the template itself and are heat-denatured to yield numerous single-stranded oligonucleotides which are of variable length but which are specific for the cognate template. Complete CviJ I* restriction of the small plasmid pUC19 (2689 bp) theoretically yields 314 oligonucleotides after a heat-denaturation step. The ability to generate numerous oligonucleotides with perfect sequence specificity is an unusual result of the use of this class of enzyme according to the present invention. Such oligonucleotides are uniquely suited for the purposes of labeling DNA, as described below.

One application of CviJ I* restriction-generated oligonucleotides is to directly label them, using conventional methods. There are several important advantages in using CviJ I* restriction-generated oligonucleotides. Conventional methods employing synthetic oligonucleotides for detection purposes generally use one oligonucleotide containing one or a few labels. A complete CviJ I* digest generates hundreds of oligonucleotides from a given template, depending on the size of the template, and thus makes hundreds of sites available for labeling, regardless of the labeling scheme utilized. These hundreds of sequence specific restriction-generated oligonucleotides have two important advantages over conventional probes used in nucleic acid detection methods. First, the generation of multiple oligonucleotide probes directed at multiple sites in a given target (theoretically, 314 sites in pUC19) provides enhanced detection sensitivities compared to synthetic oligonucleotides which are directed at 1 or a few sites in a target. The numerous labeled restriction-generated oligonucleotides represent a 10–100 fold amplification of the signal for detection compared to the use of a single oligonucleotide. Second, the short length of the restriction-generated oligonucleotides permits more efficient hybridization. This is important for two reasons. First, hybridization times using restriction-generated oligonucleotides is reduced to 1 hr as opposed to an overnight incubation with conventional probes hundreds of nucleotides in length. This is a very important advantage when using oligonucleotide probes in clinical settings. Second, the penetration of probes into permeabilized cells is a critical issue for in situ hybridization procedures. The smaller the probe, the easier the entry into the cell. Thus, the use of multiple oligonucleotide probes generated by the two base cutters greatly improves the sensitivity of in situ hybridization, a technique of considerable importance in research and clinical labs. Finally, when using membrane-based hybridization procedures, only small sections of a target nucleic acid are exposed and available for hybridization. Multiple oligonucleotides derived from a cognate template exhibit better detection sensitivities compared to long probes.

Another application of restriction-generated oligonucleotides for labeling is to employ them as primers in a polymerase extension labeling reaction in conjunction with a repetitive thermal cycling regimen of denaturation, annealing, and extension. Thermal Cycle Labeling (TCL) is a method for efficiently labeling double-stranded DNA while simultaneously amplifying large amounts of the labeled probe. The TCL system employs the two base recognition endonuclease CviJ I* to generate sequence-specific oligonucleotides from the template DNA itself. These oligonucleotides are combined with the intact template and subjected to repeated cycles of denaturation, annealing, and extension by a thermostable DNA polymerase from, for example, Thermus flavus. A radioactive- or non-isotopically-labeled deoxynucleotide triphosphate is incorporated during the extension step for subsequent detection purposes. The amplified, labeled probes represent a very heterogeneous mixture of fragments, which appears as a large molecular weight smear when analyzed by agarose gel electrophoresis. Primer-primer amplification, a side product of this reaction (produced by leaving out the intact template in the TCL reaction), may result in enhanced detection sensitivity, perhaps by forming branched structures. Biotin-labeled probes generated by the TCL protocol detect as little as 25 zeptomoles ($2.5 \times 10^{-20}$ moles) of a target sequence. A 50 µl TCL reaction yields as much as 25 µg of labeled DNA, enough to probe 25 to 50 Southern blots. After 20 cycles of denaturation and extension, biotin-dUTP-incorporated TCL probes may be routinely detected at a 1:$10^6$ dilution, which is 1000 fold more sensitive than RPL, and indicates that a significant degree of net synthesis or amplification of the probe is occurring. In addition, non-isotopically-labeled TCL probes exhibit a 10-fold improvement in detection sensitivity when compared to RPL-generated probes. $^{32}$P-labeled probes generated by the TCL protocol may also detect as little as 50 zeptomoles ($2.5 \times 10^{-20}$ moles) of a target sequence. As little as 10 pg of template DNA is enough to synthesize 5–10 ng of radiolabeled probe, which is sufficient for screening 5 Southern blots. This radioactive version of TCL generates probes having extremely high specific activities, e.g. (1–2× $10^{10}$ cpm/µg DNA), which permits 5 to 10-fold lower detection limits than conventional labeling protocols.

There are several advantages to using restriction-generated oligonucleotides for primer extension labeling of DNA. One advantage is the specificity of the primers. All of the oligonucleotides generated by the TCL system are specific for the template utilized, unlike random primer labeling (RPL) which utilizes synthetic oligonucleotides 6–9 bases in length having a random sequence. The amount of primer required for efficient labeling with the TCL system is only 10 ng, compared to the 10 µg of random primers utilized for RPL. Due to their short length, random primers anneal very inefficiently above 25°–37° C., thus RPL is limited to DNA polymerases such as Klenow or T7. The size of the restriction-generated oligonucleotides are longer than the random primers, which extends the hybridization and extension conditions to include a wide variety of temperatures and polymerases. Thus, the use of the restriction-generated sequence-specific oligonucleotides results in more efficient hybridization and extension as compared to RPL. The TCL system has been optimized for labeling with a thermostable DNA polymerase which allows the option of temperature cycling. After 20 cycles of denaturation and extension, a significant amount of amplified TCL probes can be generated. Most importantly, TCL-labeled probes exhibit a 10 fold improvement in detection sensitivity when compared to RPL-generated probes.

EXAMPLE 1

Analysis of CviJ I* Recognition Sequences

The CviJ I* recognition sequence was deduced by cloning and sequencing CviJ I* restricted pUC19 DNA fragments as described in detail in Example 8. A complete CviJ I* digest of pUC19 was ligated to an M13mp18 cloning derivative for nucleotide sequence analysis. The sequence of the entire insert was read in order to determine which sites were or were not utilized. A total of 100 clones were sequenced, resulting in 200 CviJ I* restricted junctions, the data for which are compiled in Table 1.

TABLE 1

Distribution of CviJ I* Sites as Assayed by Cloning and Sequencing

| Classification Group | NGCN Recognition Sequence | CviJ I* Sites Found in pUC19 (%) | | CviJ I* Sites Cleaved (%) | | Sites Not Cleaved (%) | | Pu/Py Structure |
|---|---|---|---|---|---|---|---|---|
| Normal (N) | A C | AGCC | 9 (4.4) | 23 | (11.5) | 1 | (0.9) | PuPuPyPy |
| | GC | GGCC | 11 (5.4) | 24 | (12.0) | 1 | (0.9) | |
| | G T | GGCT | 10 (4.9) | 13 | (6.5) | 0 | (0.0) | |
| | | AGCT | 15 (7.3) | 35 | (17.5) | 0 | (0.0) | |
| | | | 45 (22.0) | 95 | (47.5) | 2 | (1.7) | |
| Relaxed (R1) | C C | CGCC | 11 (5.4) | 11 | (5.5) | 4 | (3.5) | PyPuPyPy |
| | GC | TGCC | 12 (5.9) | 13 | (6.5) | 10 | (8.6) | |
| | T T | TGCT | 10 (4.9) | 10 | (5.0) | 5 | (4.3) | |
| | | CGCT | 22 (10.7) | 17 | (8.5) | 7 | (6.0) | |
| | | | 55 (26.9) | 51 | (25.5) | 26 | (22.4) | |
| Relaxed (R2) | A A | AGCA | 16 (7.3) | 13 | (6.5) | 5 | (4.3) | PuPuPyPu |
| | GC | GGCA | 8 (3.9) | 11 | (5.5) | 3 | (2.6) | |
| | G G | AGCG | 11 (5.4) | 12 | (6.0) | 11 | (9.5) | |
| | | GGCG | 22 (10.7) | 18 | (9.0) | 8 | (6.9) | |
| | | | 57 (27.8) | 54 | (27.0) | 27 | (23.3) | |
| Relaxed (R3) | C A | CGCA | 10 (4.9) | 0 | | 12 | (10.4) | PyPuPyPu |
| | GC | TGCA | 13 (6.3) | 0 | | 19 | (16.4) | |
| | T G | CGCG | 10 (4.9) | 0 | | 27 | (23.3) | |
| | | TGCG | 15 (7.3) | 0 | | 3 | (2.6) | |
| | | | 48 (23.4) | 0 | | 61 | (52.6) | |
| | | Total | 205 | 200 | | 116 | | |

The dinucleotide GC is found at 205 sites in pUC19. These GC sites can be divided into four classes based on their flanking Pu/Py structure, the normal recognition sequence (N) and three potential classes of relaxed sites (R1–3). As seen in Table 1, the fraction of such NGCN sites which belong to each classification is roughly equal (22.0%–27.8%). A total of 200 CviJ I* restricted junctions were analyzed by sequencing 100 cloned inserts. If CviJ I* cleaved at all NGCN sites without sequence preferences, it would be expected that the fraction of each classification should be restricted approximately equally. Instead, most of the sites cleaved by this treatment were found to be normal, or PuGCPy sites (47.5%). R1 (PyGCPy) and R2 (PuGCPu)

restricted sites were found at nearly the same frequency (25.5% and 27.0%, respectively). Out of 200 CviJ I* junctions, no R3 (PyGCPu) restricted sites were found. Thus, CviJ I* cleaves all NGCN sites except for PyGCPu. As CviJ I* cleaves 12 out of 16 possible NGCN sites, it may be referred to as a 2.25-base recognition endonuclease.

In addition to the restricted sites, those sites which were not cleaved by CviJ I* conditions were also compiled for analysis, as shown in Table 1. A total of 116 non-cleaved NGCN sites were found in the 100 inserts which were sequenced. PyGCPu sites represented the largest class of non-cleaved sites (52.6%). In only two cases were PuGCPy sites found not to be cleaved. An approximately equal fraction of R1 and R2 sites were not cleaved as were found cleaved (22.4% versus 25.5% for R1 and 23.3% versus 27.0% for R2). Based on the frequency of cleavage, or lack thereof, a hierarchy of restriction under CviJ I* conditions is evident, where PuGCPy>>PuGCPu=PyGCPy.

EXAMPLE 2

CviJ I* Restriction Generated Oligonucleotides

Due to the high frequency of CviJ I or CviJ I* restriction, it is possible to generate oligonucleotides after a heat denaturation step as described above. The size and number of the resulting oligonucleotides are important for subsequent applications such as those described above. If for example, an oligonucleotide is to be used with a large genome, it has to be long enough so that the sequence detected has a probability of occurring only once in the genome. This minimum length has been calculated to be 17 nucleotides for the human genome (Thomas, C. A., Jr. *Prog. Nucl. Acid Res. Mol. Biol.*, 5:315 (1966)). Oligonucleotides used for sequencing or PCR amplification are generally 17–24 bases in length. Oligomers of shorter length will often bind at multiple positions, even with small genomes, and thus will generate spurious extension products. Thus, an enzymatic method for generating oligomers should ideally result in polymers greater than 20 bases in length.

Figure 1B:
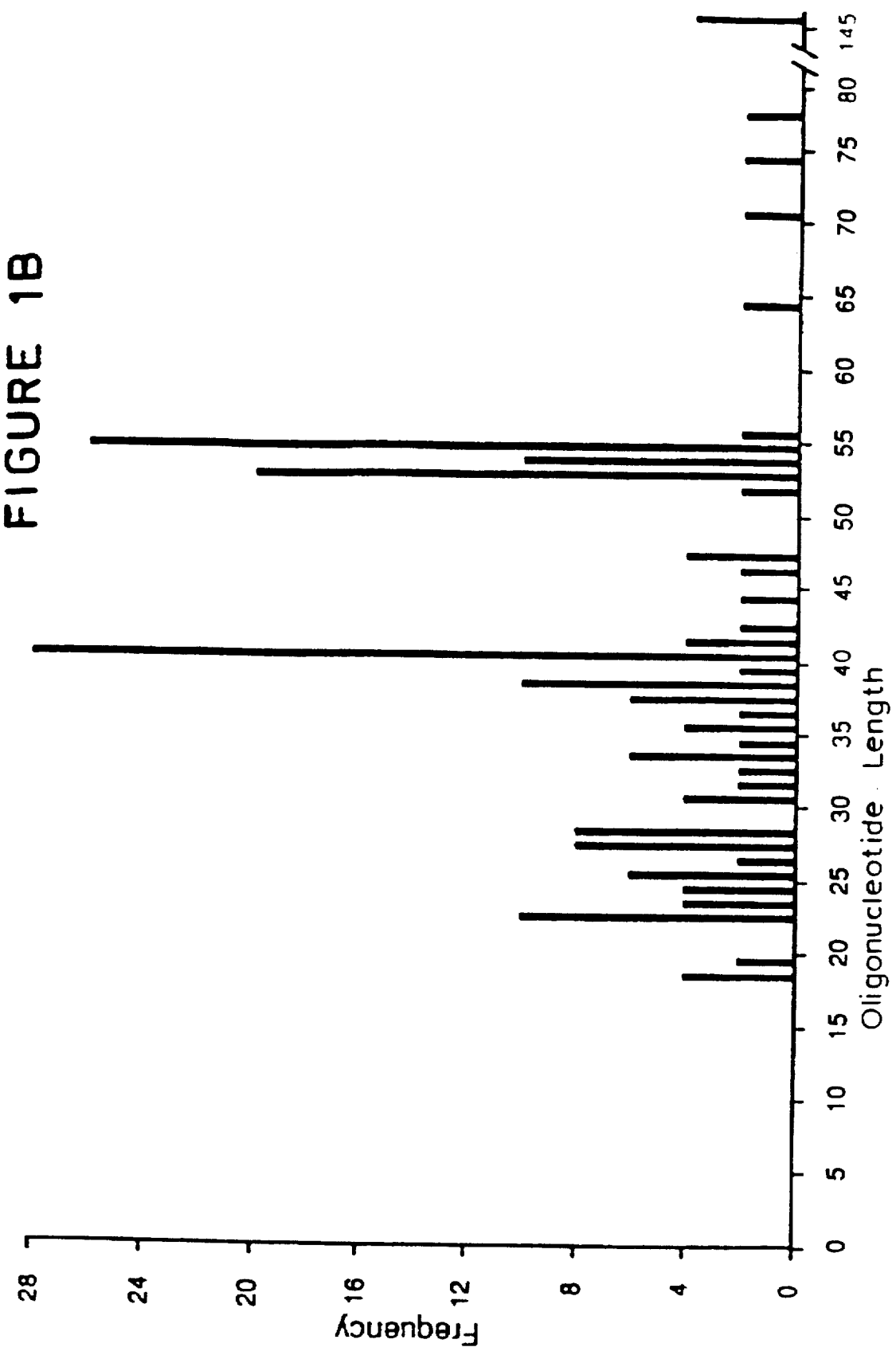
FIG. 1B is a graphic representation of the frequency and distribution of oligonucleotide fragments generated by CviJ I* digestion of pUC19.

The theoretical number of pUC19 CviJ I* restriction-generated oligomers is 314 (157 CviJ I* restriction fragments×2 oligomers/fragment), the size distribution of which is shown in panel A of FIG. 1. Most of the expected CviJ I* restriction-generated oligomers (about 75%) are smaller than 20 bp. This assumes that CviJ I is capable of restricting DNA to very small fragments, the shortest of which would be 2 bp. However, in practice, about 93% of the cloned CviJ I* fragments were 20–56 bp in size, and 3% of the fragments generated by CviJ I* were smaller than 20 bp (panel B of FIG. 1). This suggests that CviJ I* is not able to bind or restrict those fragments below a certain threshold length. Since the smallest observed fragment is 18 bp, it may be assumed that this length is the minimal size which can be generated from a given larger fragment. Whatever the reason for this phenomenon, CviJ I* treatment of DNA produces a relatively small range of oligomers (mostly 20–60 bases in length), most of which are a perfect size class for molecular biology applications.

EXAMPLE 3

Purification of CviJ I Restriction Endonuclease from IL-3A-Infected Chlorella Cells CviJ I was prepared by a modification of the method described by Xia et al., *Nucl. Acids Res.* 15:6025–6090 (1987). *Chlorella* NC64A cells (ATCC Accession No. 75399 deposited on Jan. 21, 1993, American Type Culture Collection, Rockville, Md.) were infected with the virus IL-3A (ATCC Accession No. 75354 deposited Nov. 6, 1992, American Type Culture Collection, Rockville, Md.) according to Van Etten et al., *Virology* 126:117–125 (1983). Five grams of IL-3A infected *Chlorella* NC64A cells were suspended in a glass homogenization flask with 15 g of 0.3 mm glass beads in buffer A (10 mM Tris-HCl pH 7.9, 10 mM 2-mercaptoethanol, 50 μg/ml phenylmethylsulfonyl fluoride (PMSF), 20 ug/ml benzamidine, 2 μg/ml o-phenanthroline). Cell lysis was carried out at 4000 rpm for 90 sec in a Braun MSK mechanical homogenizer (Allentown, Pa.) with cooling from a $CO_2$ tank. After lysis 2M NaCl was added to a final concentration of 200 mM, after which 10% polyethyleneimine (PEI) (Life Technologies, Bethesda, Md.) (pH 7.5) was added to a final concentration of 0.3%. The mixture was then stirred for 2 hrs. at 4° C. then centrifuged for 1 hr. at 50,000 g. Ammonium sulfate was added to the supernatant to 70% saturation and stirred overnight. A protein pellet was recovered by centrifugation for 1 hr. at 50,000 g. The resulting pellet was dissolved in 20 ml of buffer B (20 mM Tris-acetate pH 7.5, 0.5 mM EDTA, 10 mM 2-mercaptoethanol, 10% glycerol, 30 mM KCl, 50 ug/ml PMSF, 20 μg/ml benzamidine [Sigma, St. Louis, Mo.,], 2 μg/ml o-phenanthroline [Sigma]) and dialysed against 500 ml of buffer B with 3 changes. The dialysed solution was then applied to 1×6 cm Heparin-Sepharose (Pharmacia LKB, Piscataway, N.J.) column. After a 50 ml wash with buffer B, a 100 ml gradient of 0 to 0.7M KCl in buffer B was run. Fractions having CviJ I activity as measured by digestion of pUC19 DNA and agarose gel electrophoresis, were pooled, diluted in 5 volumes of buffer C (10 mM K/PO4 pH 7.4, 0.5 mM EDTA, 10 mM 2-mercaptoethanol, 75 mM NaCl, 0.05% Triton X-100, 10% glycerol, 50 μg/ml PMSF, 20 μg/ml benzamidine, 2 μg/ml o-phenanthroline) and applied to a 1×7 cm Phosphocellulose P11 (Whatman) column equilibrated in buffer C. After washing with 30 ml of buffer C, CviJ I was eluted by a 100 ml gradient of 0 to 0.7M NaCl in buffer C. At this step CviJ I activity separated from non-specific nucleases. CviJ I containing fractions were pooled and diluted in 4 volumes of buffer C and applied to a 1×4 cm hydroxyapatite HTP column (BioRad, Hercules, Calif.). After washing with 30 ml of buffer C, CviJ I was eluted by a 0 to 0.7M potassium phosphate (pH 7.4) gradient in buffer C. Active fractions containing CviJ I activity and lacking non-specific nuclease activity were pooled and were dialysed overnight against storage buffer (50 mM potassium phosphate 200 mM KCl, 0.5 mM EDTA, 50% glycerol, 20 ug/ml PMSF were pooled) and stored at −20° C.

EXAMPLE 4

Quasi-Random Fragmentation of DNA

Shotgun cloning and sequencing requires the generation of an overlapping population of DNA fragments. Therefore, conditions were established for the partial digestion of DNA with CviJ I to yield an apparently random pattern, or smear, of fragments in the appropriate size range. Conventional methods for obtaining partially restricted DNA include limiting the incubation time or limiting the amount of enzyme used in the digestion. Initially, agarose gel electrophoresis and ethidium bromide staining of the treated DNA were utilized to assess the randomness and size distribution of the fragments.

CviJ I was obtained frown CHIMERx (Madison, Wis.) where it was prepared as described in Example 3. Digestion of pUC19 DNA for limited time periods, or with limiting amounts of CviJ I under normal or relaxed conditions, did not produce a quasi-random restriction pattern, or smear. Instead, a number of discrete bands were observed, as shown in FIG. 2, lane 3 for the CviJ I* partial digestion of pUC19. Complete digests of pUC19 under normal and CviJ I* buffer conditions are shown in lanes 1 and 2 respectively. These results show that, under these relaxed conditions, CviJ I has a strong restriction site preference.

To eliminate the apparent restriction site preferences observed under the partial restriction conditions described above, a series of altered reaction conditions were explored. Conditions of high pH, low ionic strength, addition of solvents such as glycerol or dimethylsulfoxide, and/or substitution of $Mn^{2+}$ for $Mg^{2+}$ were systematically tested with CviJ I endonuclease using the plasmid pUC19. FIG. 2 shows the results of these tests. In Lane M, a 100 bp DNA ladder was run. In Lanes 1–4, pUC19 DNA (1.0 µg) was run after digestion at 37° C. in a 20 µl volume for the following times and conditions: Lane 1, complete CviJ I digest (1 unit of enzyme for 90 min in 50 mM Tris-HCl, pH 8.0, 10 mM $MgCl_2$, 50 mM NaCl); Lane 2, complete CviJ I* digest (1 unit of enzyme for 90 min in 50 mM Tris-HCl, pH 8.0, 10 mM $MgCl_2$, 50 mM NaCl, 1 mM ATP, 20 mM DTT); Lane 3, partial CviJ I* digest (0.25 units of enzyme for 30 min in 50 mM Tris-HCl, pH 8.0, 10 mM $MgCl_2$, 50 mM NaCl, 1 mM ATP, 20 mM DTT); Lane 4, partial CviJ I** digest (0.5 units of enzyme for 60 min in 10 mM Tris-HCl, pH 8.0, 10 mM $MgCl_2$, 10 mM NaCl, 1 mM ATP, 20 mM DTT, 20% v/v DMSO); and Lane 5, uncut pUC19 (1.0 µg).

The digestion condition which yielded the best "smearing" pattern was obtained when the ionic strength of the relaxed reaction buffer was lowered and an organic solvent was added (FIG. 2, lane 4). Plasmid pUC19 partially digested under these conditions yields a relatively non-discrete smear. This activity is referred to as CviJ I** to differentiate it from the originally-characterized star activity described in Xia et al., *Nucl. Acids Res.* 15:6075–6090 (1987). The appearance of diffuse, hint bands overlying a background smear generated from this 2686 bp molecule indicates that some weakly preferred or resistant restriction sites may bias the results of subsequent cloning experiments.

DNA was mechanically sheared by sonication utilizing a Heat Systems Ultrasonics (Farmingdale, N.Y.) W-375 cup horn sonicator as specified by Bankier et al., *Methods in Enzymology* 155:51–93 (1987). DNA fragmented by this method has random single-stranded overhanging ends (ragged ends).

CviJ I* digested and sonicated samples were size fractionated by agarose gel electrophoresis and electroelution, or by spin columns packed with the size exclusion gel matrix, Sephacryl S-500 (Pharmacia LKB, Piscataway N.J.) to eliminate small DNA fragments. Spin columns (0.4 cm in diameter) were packed to a height of 1.3 cm by adding 1 ml of Sephacryl S-500 slurry and centrifuging at 2000 RPM for 5 minutes in a Beckman CPR centrifuge. The columns were rinsed 3 times with 1 ml aliquots of 100 mM Tris-HCl (pH 8.0) by centrifugation at 2000 RPM for 2 min. Typically, 0.2–2.0 µg of fragmented DNA in a total volume of 30 µl was applied to the column. The void volume, containing the larger DNA fragments, was recovered in the column eluant after spinning at 2000 RPM for 5 minutes. The capacity of this micro-column procedure is 2 µg of DNA. Agarose gel electrophoresis and electroelution are described in detail by Sambrook et al. *Molecular Cloning: A Laboratory Manual*, Second Edition Cold Spring Harbor Laboratory Press, Cold Spring Harbor N.Y. (1989) and is well known to those skilled in the art. In these experiments, 5 µg of sample was pipetted into a 2 cm-wide slot on a 1% agarose gel. Electrophoresis was halted after the bromophenol blue tracking dye had migrated 6 cm. Fragments larger than 750 bp, as judged by molecular size markers, were separated from smaller sizes and electrophoresed onto dialysis tubing (1000 MW cutoff). The fractionated material was extracted with phenol-chloroform and precipitated using ice cold ethanol (50% final volume) and ammonium acetate (2.5M final concentration).

The ragged ends of the sonicated DNA were rendered blunt utilizing two different end repair reactions. In one end repair reaction (ER 1) sonicated DNA was treated according to the procedure outlined by Bankier et al. *Methods in Enzymology* 155:51–93 (1987), where 2.0 µg of sonicated lambda DNA is combined with 10 units of the Klenow fragment of DNA polymerase I, 10 units T4 DNA polymerase, 0.1 mM dNTPs, (deoxynucleotide triphosphates=deoxyadenosine triphosphate, deoxthymidine triphosphate, deoxycytosine triphosphate, and deoxyguanosine triphosphate) and reaction buffer (50 mM Tris-HCl, pH 7.5, 10 mM $MgCl_2$, 10 mM DTT). This mixture was incubated at room temperature for 30 min followed by heat denaturation of the enzymes at 65° C. for 15 minutes. In a second end repair reaction (ER 2), an excess of the reagents and enzymes described above were utilized to ensure a more efficient conversion to blunt ends. In this reaction, 0.2 µg of the sonicated lambda DNA sample was treated under the same reaction conditions described above.

Figure 3:
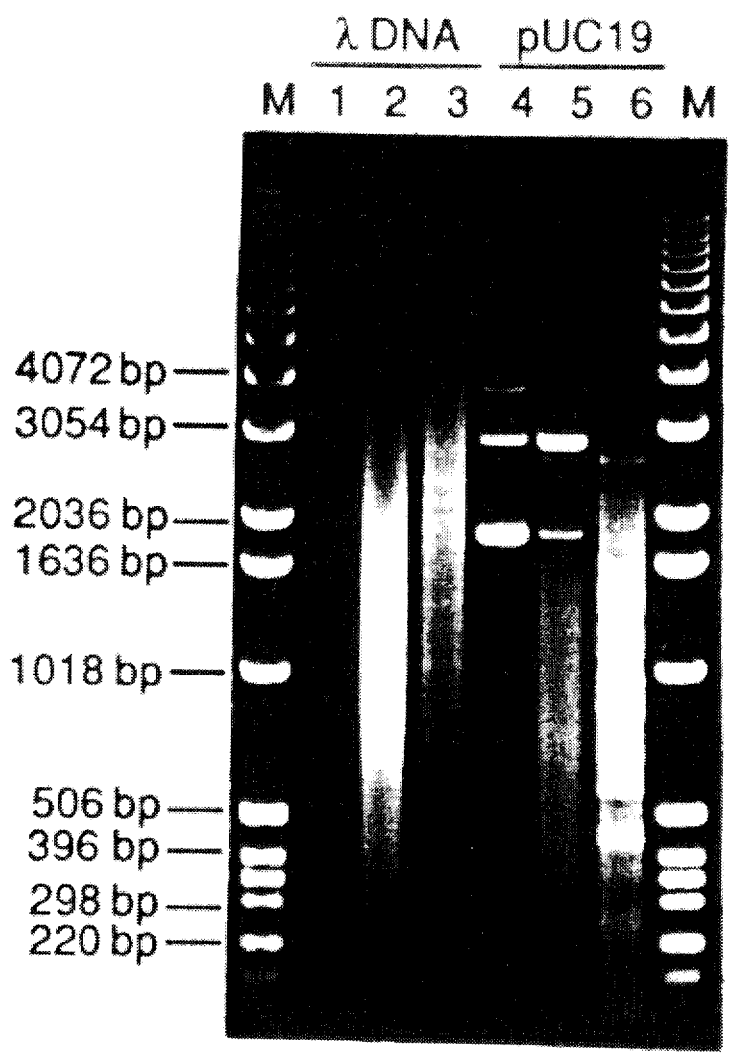
FIG. 3 is a photographic reproduction of a gel depicting comparisons of sonicated versus CviJ I** partially digested DNAs.

FIG. 3 shows comparisons of the size distributions of sonicated DNA vs. DNA that was partially digested with CviJ I. In Lanes M, a 1 kb DNA ladder was run. In Lanes 1–3, untreated λ DNA (0.25 µg), sonicated λ DNA (1.0 µg), and CviJ I partially-digested λ DNA (1.0 µg) were run, respectively. In Lanes 4–6, untreated pUC19 (0.25 µg), sonicated pUC19 (1.0 µg), and CviJ I** partially-digested pUC19 (1.0 µg) were run, respectively.

Fragmentation of a large substrate such as lambda DNA (45 kb) revealed essentially no banding differences between the CviJ I method and sonication, as demonstrated in FIG. 3, lanes 2 and 3. In addition, pUC19 DNA that was partially digested with CviJ I gave a size distribution or "smear" that closely resembled that achieved with sonication (FIG. 3, lanes 5 and 6). As expected, the minor bias evident with a small molecule such as pUC19 was not detectable with a larger substrate such as lambda DNA.

The intensity and duration of sonic treatment affects the size distribution of the resulting DNA fragments. The results obtained from the sonication of lambda and pUC19 samples (FIG. 3) were obtained from three 20 second pulses at a power setting of 60 watts. Sonication-generated smears are similar, although the size distribution of fragments is consistently greater with CviJ I** fragmentation. This result favors the cloning of larger inserts, which facilitates the efficiency of end-closure strategies (Edwards et al., *Genome* 6:593–608 (1990)). The size distribution of the DNA fragmented by CviJ I** is controlled by incubation time and amount of enzyme, variables which are readily optimized by routine analysis. An excess of enzyme or a long incubation time will completely digest pUC19 DNA, resulting in fragments which range in size from approximately 20 bp to approximately 150 bp (FIG. 2, lanes 1 and 2). The results shown in FIG. 3 were obtained by incubating pUC19 for 40 minutes and lambda DNA for 60 minutes with 0.33 units of CviJ I/µg substrate. The efficiencies of the two methods for randomly fragmenting DNA were quantitatively analyzed for use in molecular cloning, as described below.

EXAMPLE 5

Rapid DNA Size Fractionation Utilizing Spin Column Chromatography

The amount of data obtained by the shotgun sequencing approach is substantially increased if fragments of less than 500 bp are eliminated prior to the cloning step. Small fragments yield only a portion of the sequence data which may be collected from polyacrylamide gel based separations and, thus, such small fragments lower the efficiency of this strategy. Agarose gel electrophoresis followed by electroelution is commonly used to size fractionate DNA prior to shotgun cloning (Bankier et al., Methods in Enzymol. 155:51–93 (1987)). Approximately three hours are required to prepare the agarose gel, electrophorese the sample, electroelute fragments larger than 500 bp, perform phenol-chloroform extractions, and precipitate the resulting material.

Figure 4A:
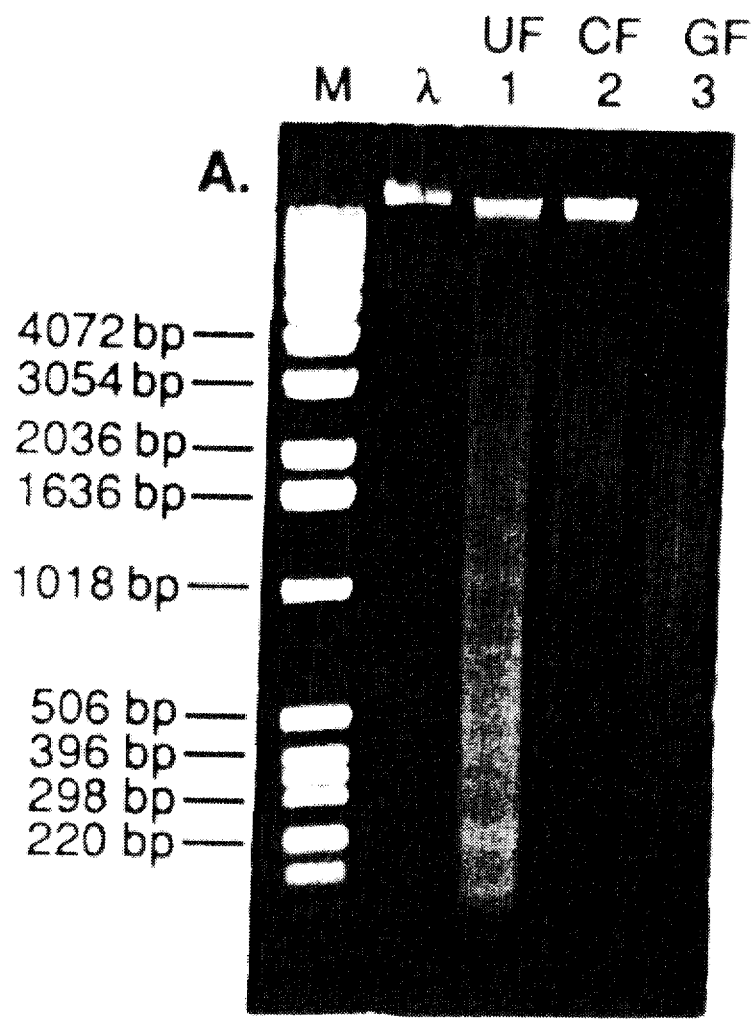
FIG. 4A is a photographic reproduction of an agarose gel electrophoresis analysis of size fractionated DNA by micro-column chromatography compared to fractionation by agarose gel electroelution.

The results of 5 out of 9 independent trials size-fractionating CviJ I-fragmented lambda DNA by agarose gel electrophoresis are shown in FIGS. 4A–E. FIGS. 4A–D illustrate the following. In FIG. 4A: Lane M, 1 kb DNA ladder; lane λ, untreated λ DNA (0.25 μg); lane 1, unfractionated (UF) CviJ I partially-digested λ DNA (1.0 μg); lane 2, column-fractionated (CF) CviJ I partially-digested λ DNA (1.0 μg); lane 3, gel-fractionated (GF) CviJ I partially-digested λ DNA (1.0 μg); and in FIGS. 4B–E are additional trials of the same treatments as in the lanes of FIG. 4A which have the same label.

Small DNA fragments may also be removed by passing the sample through a short column of Sephacryl S-500. Approximately 15 min. are needed to prepare the column and 5 min. to fractionate the DNA by this method.

Figure 4B:
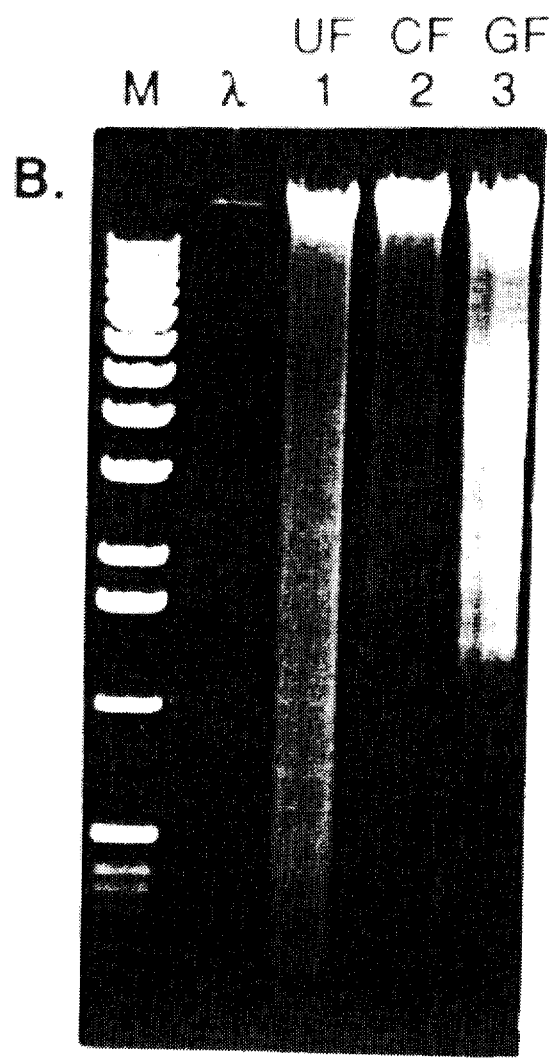
FIGS. 4B–E. Additional trials of the same treatment used in FIG. 4A.
Figure 4C:
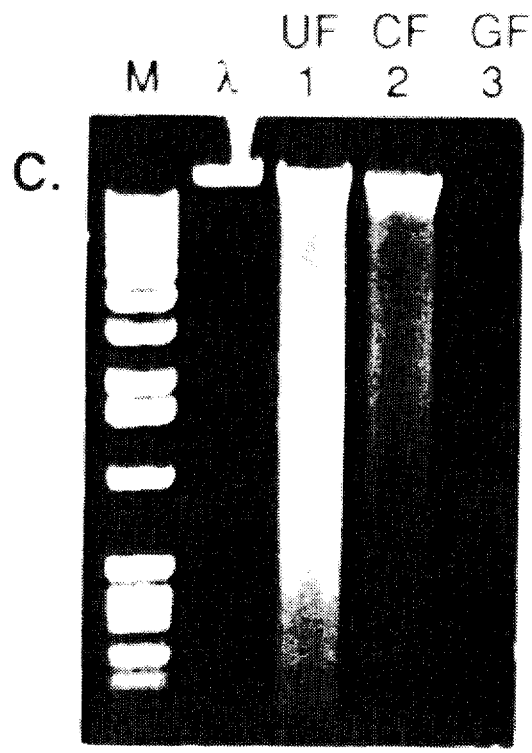
Figure 4D:
Figure 4E:

The results of three out of nine trials using a Sephacryl S-500 column are shown in FIGS. 4A–C. The efficiency of eliminating small DNA fragments (<500 bp) by spin column chromatography appears high, and the reproducibility was excellent. This result is in contrast to the agarose gel electrophoresis and electroelution data presented in FIGS. 4A–E wherein nine replicate trials of this method yielded nine differently sized products, regardless of the source of the agarose. Both methods yielded 30–40% recoveries as measured by UV spectrophotometry. To quantitate the relative efficiencies of the two fractionation methods, the lambda DNA size fractionated in FIG. 4A lanes 2 and 3, and FIG. 4B lane 3 were analyzed for cloning efficiency and insert size, as described below.

EXAMPLE 6

Cloning Efficiencies of Gel Elution and Chromatography Fractionation Methods The efficacy of size selection was quantified by two criteria: 1) by comparing the relative cloning efficiency of CviJ I** partially-digested lambda DNA fragments fractionated either by agarose gel electrophoresis and electroelution or micro-column chromatography, and 2) determining the size distribution of the resulting cloned inserts. To reduce potential variables, large quantities of the cloning vector and ligation cocktail were prepared, ligation reactions and transformation of competent E. coli were performed on the same day, numerous redundant controls were performed, and all cloning experiments were repeated twice. Ligation reactions were carried out overnight at 12° C. in 20 μl mixtures using the following conditions: 25 mM Tris-HCl (pH 7.8), 10 mM $MgCl_2$, 1 mM DTT, 1 mM ATP, DNA, and 2000 units of T4 DNA ligase. For unfractionated samples, 10 ng of fragments and 100 ng of Hinc II-restricted, dephosphorylated pUC19 were combined under the above conditions. For Sephacryl S-500 fractionated samples, 50 ng of size-selected fragments were ligated with 100 ng of Hinc II-restricted, dephosphorylated pUC19. This increase in fractionated DNA was determined empirically to compensate for the lower concentration of "ends" resulting from the fractionation procedure and/or the lowered efficiency of cloning larger fragments. Ligation reaction products were added to competent E. coli DH5αF' (φ80dlacZΔM15 Δ(lacZYA-argF)U169 deoR gyrA96 recA1 relA1 endA1 thi-1 hsdR17($r_K^-$, $m_K^+$) supE44 λ–) in a transformation mixture as specified by the manufacturer (Life Technologies, Bethesda, Md.) and aliquots of the transformation mixture were plated on T agar (Messing, Methods in Enzymol. 101:20–78 (1983)) containing 20 μg/ml ampicillin, 25 μl of a 2% solution of isopropylthiogalactoside (IPTG) and 25 μl of a 2% solution of 5-dibromo-4-chloro-3-indolylgalactoside (X-GAL). The cloning efficiencies reported are the average of triplicate platings of each ligation reaction. The concentration of the fractionated material was checked spectrophotometrically so that 50 ng was added to all ligation reactions. This material was ligated to Hinc II-digested and dephosphorylated pUC19. This cloning vector was chosen because it permits a simple blue to white visual assay to indicate whether a DNA fragment was cloned (white) or not (blue) (Messing, Methods in Enzymol. 101:20–78 (1983)).

A summary of the cloning efficiencies calculated from two independent trials is given in Table 2.

TABLE 2

Cloning Efficiencies of CviJ I** Partially Digested Lambda DNA Fractionated by Microcolumn Chromatography Versus Agarose Gel Electroelution.

| | Trial I | | Trial II | |
| --- | --- | --- | --- | --- |
| | Colony Phenotype | | | |
| DNA/treatment | Blue | White | Blue | White |
| Supercoiled pUC19 | 55000 | <10 | 50000 | <10 |
| pUC19/Hinc III/CIAP | 210 | <1 | 320 | 1 |
| pUC19/Hinc II/CIAP/ T4 DNA ligase | 150 | 4 | 210 | 7 |
| λ/CviJ I** partial/CF + pUC19 | 140 | 240 | 210 | 240 |
| λ/CviJ I** partial/ GFE1 + pUC19 | 98 | 49 | 200 | 18 |
| λ/CviJ I** partial/ GFE2 + pUC19 | 82 | 54 | 95 | 74 |

Cloning efficiencies reflect the number of ampicillin-resistant colonies/ng pUC19 DNA. CIAP represents treatment with calf intestinal alkaline phosphatase used to dephosphorylate Hinc II-digested pUC19 to minimize self-ligation. CF refers to DNA that was fractionated on Sephacryl S-500 columns as described above. GFE1 and GFE2 refer to two runs wherein DNA was fractionated by agarose gel electrophoresis and electroeluted. λ refers to bacteriophage λ DNA.

These trials represent repeated experiments in which λ DNA fragments generated by CviJ I** partial digestion were ligated to Hinc II-linearized, dephosphorylated pUC19 and transformed into DH5α F' competent cells described above.

The first three rows in Table 2 show controls performed to establish a baseline to better evaluate the various treatments. Supercoiled pUC19 transforms *E. coli* 10 times more efficiently than the Hinc II-digested plasmid and 150–260 times more efficiently than the Hinc II-digested and dephosphorylated plasmid. The number of blue and white colonies which resulted frown transforming Hinc II-cut and dephosphorylated pUC19 was determined both before and after treatment with T4 DNA ligase in order to differentiate these background events from cloning inserts. The background of blue colonies (which represent the uncut and/or non-dephosphorylated population of molecules) averaged 0.4%, compared to supercoiled plasmid. The background of white colonies (which presumably results from contaminating nucleases in the enzyme treatments or genomic DNA in the plasmid preparations) after Hinc II-digestion, dephosphorylation, and ligation of pUC19 averaged 0.014% as compared to the supercoiled plasmid.

The number of white colonies obtained when microcolumn fractionated DNA was cloned into pUC19 was 240 ng vector in both trials. The efficiency of cloning gel fractionated and electroeluted DNA ranged from 18–74 white colonies/ng vector. The data show that column fractionated DNA results in three to thirteen times the number of white colonies, and presumably recombinant inserts, as gel fractionated and electroeluted DNA. The size distribution of the inserts present in these white colonies is depicted in FIGS. 5A–C. In FIG. 5A, a CviJ I partial digest of 2 µg of λ DNA was size fractionated on a 4 mm by 13 mm column of Sephacryl S-500 at 2,000 x g for 5 minutes. The void volume containing partially digested DNA was directly ligated to linear, dephosphorylated pUC19 and 43 resulting clones were analyzed for insert size. The DNA for this experiment is the same as that shown in FIG. 4A, lane 2. In FIG. 5B, a CvJI partial digest of 5 µg of λ DNA was size fractionated by agarose gel electroelution. The eluted DNA was phenol-extracted and ligated to linear, dephosphorylated pUC19, and the resulting 40 clones were analyzed for insert size. The DNA for this experiment is the same as that shown in FIG. 4A, lane 3. In FIG. 5C, the procedure is the same as in 4B, except the DNA for this experiment came from FIG. 4B, lane 3.

A total of 43 random clones obtained from micro-column chromatography fractionation were analyzed for insert size (as shown in FIG. 5A). Most of these inserts were larger than 500 bp (37/43 or 86%), 11.6% (5/43) were smaller than 500 bp, and one clone (2.3%) was smaller than 250 bp. The average insert size was 1630 bp. These results are in contrast to those obtained by agarose gel fractionation (as shown in FIGS. 5B and 5C). In the first trial (FIG. 5B) most of the inserts were smaller than 500 bp (26/37 or 70.3%) and only 29.7% (11/37) were larger than 500 bp in size. In the second trial (FIG. 5C) all of the inserts (40 total) were smaller than 500 bp. Thus, the use of agarose gel electroelution for the size fractionation of DNA results in unexpectedly variable and low cloning efficiencies.

EXAMPLE 7

Cloning Sonicated and CviJ I**-Digested Lambda DNA

To compare the cloning efficiencies of sonicated and CviJ I-digested nucleic acid, λ DNA was fragmented by each of these methods and ligated to pUC19 which was linearized with Hinc II and dephosphorylated to minimize self-ligation. DNA fragmented by CviJ I digestion and sonication was cloned both before and after Sephacryl S-500 size fractionation. Sonicated lambda DNA was subjected to an end repair treatment prior to ligation. Ligations were performed as described in Example 6. One-tenth of the ligation reaction (2 µl) was utilized in the transformation procedure, and the fraction of nonrecombinant (blue) versus recombinant (white) colonies was used to calculate the efficiency of this process.

The efficacy of the methods was quantified by comparing the cloning efficiency of lambda DNA fragments generated either by sonication or CviJ I partial digestion. To reduce potential cloning differences based on size preference, the size distribution of the DNA generated by these two methods was closely matched. Other experimental details were designed to reduce potential variables, as described above. Certain variables were unavoidable, however. For example, the sonicated DNA fragments required an enzymatic step to repair the ragged ends as described in Example 1 prior to ligation, whereas the CviJ I digests were heat-denatured and directly ligated to Hinc II digested pUC19.

A summary of the cloning efficiencies calculated from two independent trials is given in Table 3, section A (unfractionated samples), and Section B (fractionated samples).

TABLE 3

Cloning Efficiencies of CviJ I** Partially Digested λ DNA Versus Sonicated λ DNA

| DNA/treatment | Trial I | | Trial II | |
|---|---|---|---|---|
| | Colony Phenotype | | | |
| | Blue | White | Blue | White |
| A. Unfractionated Samples | | | | |
| Supercoiled pUC19 | 30000 | <10 | 16000 | <10 |
| pUC19/Hinc II/CIAP | 150 | <1 | 31 | 1 |
| pUC19/Hinc II/CIAP/ T4 DNA ligase | 100 | <1 | 15 | 1 |
| λ/Alu I + pUC19 | 200 | 400 | 73 | 250 |
| λ/CviJ I** Partial + pUC19 | 100 | 160 | 97 | 340 |
| λ/Sonicated + pUC19 | — | — | 11 | 29 |
| λ/Sonicated/ER 1 + pUC19 | 17 | 10 | 10 | 44 |
| λ/Sonicated/ER 2 + pUC19 | — | — | 40 | 100 |
| B. Fractionated Samples | | | | |
| Supercoiled pUC19 | 35000 | <10 | 12000 | <10 |
| pUC19/Hinc II/CIAP | 30 | <1 | 180 | <1 |
| pUC19/Hinc II/CIAP/ T4 DNA ligase | 60 | <1 | 10 | <1 |
| λ/Alu I + pUC19 | 28 | 23 | 33 | 48 |
| λ/CviJ I** Partial + pUC19 | 31 | 90 | 36 | 68 |
| λ/Sonicated + pUC19 | 20 | 6 | 99 | 19 |
| λ/Sonicated/ER 1 + pUC19 | 27 | 32 | 40 | 19 |
| λ/Sonicated/ER 2 + pUC19 | — | — | 25 | 63 |

Cloning efficiencies represent the number of ampicillin-resistant colonies/ng pUC19 DNA. CIAP indicates treatment with calf intestinal alkaline phosphatase. ER1 and ER2 are end repair methods described in Example 4. λ refers to bacteriophage lambda.

The indicated trials represent repeated experiments in which two identical sets of lambda DNA fragments generated by Alu I complete digestion, CviJ I** partial digestion, or sonication were each ligated to Hinc II-linearized, dephosphorylated pUC19 and transformed into DH5αF' competent cells. The cloning efficiencies reported are the average of triplicate platings of each ligation reaction. In case the Sephacryl S-500 size fractionation step introduced inhibitors of ligation or transformation or resulted in differences attributable to the size of the material, the sonicated and CviJ I**-digested samples were ligated with pUC19 both prior to (A) and after (B) the fractionation steps. The first three rows in Table 3, sections A and B, are controls performed to establish a baseline to better evaluate the various treatments. These data show that supercoiled pUC19 transforms E. coli 200–1000 times more efficiently than the Hinc II-restricted and dephosphorylated plasmid. Without this dephosphorylation step, the cloning efficiency is 10% that of the supercoiled molecule (data not presented). The background of blue colonies averaged 0.5% in these experiments, compared to supercoiled plasmid, while the background of white colonies averaged 0.005%.

A comparison of the data from unfractionated versus fractionated samples in Table 3, sections A and B, reveals a general decline in the number of white and blue colonies obtained after sizing. This decrease is primarily due to the fact that cloning efficiencies are dependent upon the size of the fragment, favoring smaller fragments and thus giving higher efficiencies for the unfractionated material. This is illustrated by comparing the efficiency of cloning unfractionated and fractionated λ DNA which was completely restricted with Alu I. This four base recognition endonuclease produces blunt ends and cuts λ DNA (48,502 bp) at 143 sites. Only 25 of the resulting 144 fragments (17%) are larger than 500 bp. The number of white colonies obtained when unfractionated λ DNA, completely restricted with Alu I, was cloned into pUC19 ranged from 250–400/ng vector, versus 23–48/ng vector for the fractionated material. This ten fold decrease was only noticed for the λ Alu I digests, and probably reflects the large portion of small molecular weight fragments (approximately 75%) which is excluded from the fractionated ligation reactions.

The number of white colonies obtained when unfractionated CviJ I treated λ DNA was cloned into pUC19 ranged from 160–340/ng vector, versus 68–90 white colonies/ng vector if the same material was fractionated. Unfractionated λ DNA, completely digested with Alu I, results in cloning efficiencies very similar to unfractionated CviJ I treated DNA. Sonicated λ DNA is a poor substrate for ligation, compared to CviJ I** treatment, as indicated by the roughly ten-fold reduced cloning efficiencies.

Enzymatic repair of the ragged ends produced by sonication results in an increased cloning efficiency. Using conditions described in Example 4 for the first end repair treatment (ER 1), 10–44 (fractionated) and 19–32 (unfractionated) white colonies/ng vector were observed. However, ER 1 conditions may not be optimal, as an alternate end repair reaction (ER 2) (as described in Example 4) resulted in greater numbers of white colonies (63 and 100/ng vector for fractionated and unfractionated DNA, respectively). In this reaction, a ten-fold excess of reagents and enzymes were utilized to repair the sonicated DNA, which apparently improved the efficiency of cloning such molecules by two to three fold. The data collected from multiple cloning trials in Table 3, sections A and B, show that CviJ I partial digestion results in three to sixteen times the number of white colonies than sonicated ER 1-treated DNA. Even with an optimal end repair reaction for the sonicated fragments, DNA treated with CviJ I yielded three times more white colonies.

EXAMPLE 8

Analysis of CviJ I** Fragmentation for Shotgun Cloning and Sequencing

Figure 6:
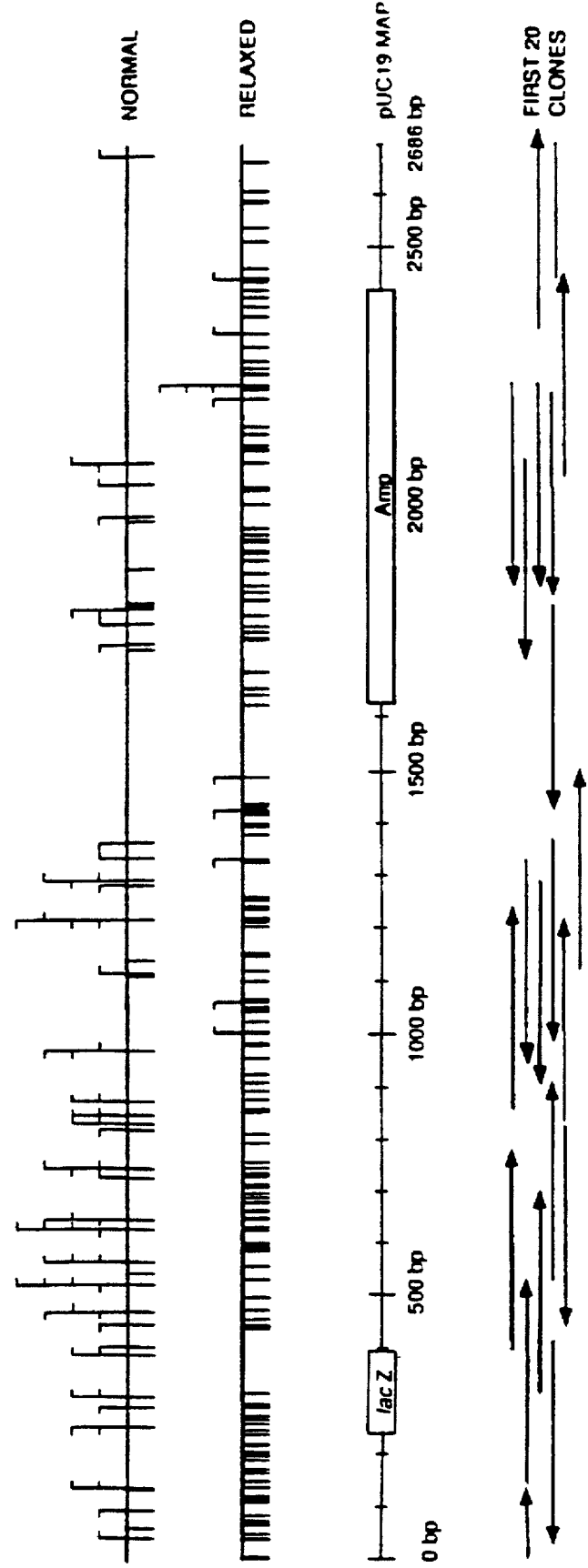
FIG. 6 is a schematic depiction of the distribution of CviJ I sites in pUC19.

The ability of CviJ I partial digestion to create uniformly representative clone libraries for DNA sequencing was tested on pUC19 DNA. pUC19 DNA was digested under CviJ I conditions and size fractionated as described above. The fractionated DNA was cloned into the EcoR V site of M13SPSI, a lacZ minus vector constructed by adding an EcoR V restriction site to wild type M13 at position 5605. M13SPSI lacks a genetic cloning selection trait, therefore after ligation of the pUC19 fragments into the vector the sample was restricted with EcoRV to reduce the background of nonrecombinant plaques. Bacteriophage M13 plaques were picked at random and grown for 5–7 hours in 2 ml of 2xTY broth containing 20 μl of a DH5αF' overnight culture. After centrifugation to remove the cells, single-stranded phage DNA was purified using Sephaglass™ as specified by the manufacturer (Pharmacia LKB, Piscataway N.J.). The single-stranded DNA was sequenced by the dideoxy chain termination method using a radiolabeled M13-specific primer and Bst DNA polymerase (Mead et al., *Biotechniques* 11:76–87 (1991)). The first 100 bases of 76 randomly chosen clones were sequenced to determine which CviJ I recognition site was utilized, the orientation of each insert and how effectively the cloned fragments covered the entire molecule, as shown in FIG. 6. The positions of the 45 normal CviJ I sites (PuGCPy) in pUC19 are indicated beneath the line labeled "NORMAL" in the FIG. 6. Similarly, the 160 CviJ I* sites (GC) are indicated beneath the line labeled "RELAXED" in FIG. 6. The marks above these lines indicate the CviJ I** pUC19 sites which were found in the set of 76 sequenced random clones. The frequency of cloning a particular site is indicated by the height of the line, and the left or right orientation of each clone is also indicated at the top of each mark. There are a total of 205 CviJ I and CviJ I* sites in pUC19.

The data presented in FIG. 6 demonstrate that, under CviJ I** partial conditions, normal CviJ I sites are preferentially restricted over relaxed (CviJ I*) sites. Of the 76 clones that were analyzed, only 13%, or 1 in 7, had sequence junctions corresponding to a relaxed CviJ I* site. Thirty-five of the forty-five possible normal restriction sites were cloned, as compared to eight of the possible one hundred sixty relaxed sites. If the enzyme had exhibited no preference for normal or relaxed sites under the CviJ I** partial conditions utilized here, then 78% of the sequence junctions analyzed should have been generated by cleavage at a relaxed CviJ I* site. It may be noted that the relaxed CviJ I* restriction sites that were found appear to be clustered in two regions of the plasmid that are deficient in normal CviJ I sites. In addition, the combined distribution of the normal and relaxed sites which were restricted to generate the 76 clones appears to be quasi-random. That is, the longest gap between cloned restriction sites was no greater than 250 bp and no one particular site is over-utilized.

A detailed analysis of the distribution of CviJ I** sequence junctions found from cloning pUC19 is presented in Table 4.

TABLE 4

Distribution of Cloned CviJ I** Partially-Digested pUC19 Sites.
NGCN

| Classification Group | Recognition Sequence | Site Distribution in pUC19 (%) | | | Cloned CviJ I** Distribution (%) | | Pu/Py Structure |
|---|---|---|---|---|---|---|---|
| Normal (N) | A C | AGCC | 9 | (4.4) | 13 | (17.1) | PuPuPyPy |
|  | G C | GGCC | 11 | (5.4) | 16 | (21.1) |  |
|  | G T | GGCT | 10 | (4.9) | 12 | (15.8) |  |
|  |  | AGCT | 15 | (7.3) | 25 | (32.9) |  |
|  |  |  | 45 | (22.0) | 66 | (86.9) |  |
| Relaxed (R$_1$) | C C | CGCC | 11 | (5.4) | 0 |  | PyPuPyPy |
|  | G C | TGCC | 12 | (5.9) | 2 | (2.6) |  |
|  | T T | TGCT | 10 | (4.9) | 1 | (1.3) |  |
|  |  | CGCT | 22 | (10.7) | 2 | (2.6) |  |
|  |  |  | 55 | (26.9) | 5 | (6.5) |  |
| Relaxed (R$_2$) | A A | AGCA | 16 | (7.3) | 1 | (1.3) | PuPuPyPu |
|  | G C | GGCA | 8 | (3.9) | 0 |  |  |
|  | G G | AGCG | 11 | (5.4) | 0 |  |  |
|  |  | GGCG | 22 | (10.7) | 4 | (5.2) |  |
|  |  |  | 57 | (27.8) | 5 | (6.6) |  |
| Relaxed (R$_3$) | C A | CGCA | 10 | (4.9) | 0 |  | PyPuPyPu |
|  | G C | TGCA | 13 | (6.3) | 0 |  |  |
|  | T G | CGCG | 10 | (4.9) | 0 |  |  |
|  |  | TGCG | 15 | (7.3) | 0 |  |  |
|  |  |  | 48 | (23.4) | 0 |  |  |

The GC sites in pUC19 may be divided into four classes based on their flanking Pu/Py structure. The fraction of GC sites observed in pUC19 which belong to each classification is roughly equal (22.0–27.8%). A striking difference was found between the observed distribution in pUC19 of normal and relaxed (R1, R2, R3) CviJ I recognition sites and the distribution revealed by shotgun cloning and sequence analysis of CviJ I**-treated DNA. While most of the sites cleaved by this treatment were found to be PuGCPy (about 87%), or "normal" restriction sites, a significant fraction of the cleavage occurred at PyGCPy (about 6.5%) and PuGCPu (about 6.6%) sites, considering the short incubation times and limiting enzyme concentrations. The latter two categories of sites, and presumably the PyGCPu sites as well, are completely restricted under "relaxed" conditions, provided an excess of enzyme is present and sufficient time is allowed (see FIG. 2, and Xia et at., *Nucleic Acids Res.* 15:6075–6090 (1987)).

Digestion using CviJ I treatment results in a relatively even distribution of breakage points across the length of the molecule (as shown in FIG. 6). As described above, FIG. 6 depicts a linear map of pUC19 showing the relative position of the lacZ' gene (α peptide of β-galactosidase gene) and ampicillin resistance gene (Amp). The marks extending beneath the top line (labeled "NORMAL") show the relative position of the 45 normal CviJ I sites (PuGCPy) present in pUC19. The marks above the line are the cleavage sites found from sequencing the CviJ I partial library. The height of the line indicates the number of clones obtained from cleavage at that site, and the orientation of the flag designates the right or left orientation of the respective clone. The marks extending beneath the second line (labeled "RELAXED") show the relative positions of the 160 CviJ I* sites (GC) present in pUC19. Those marks above the line were found from sequencing the CviJ I partial library. The bottom portion of FIG. 6 shows the relative position and orientation of the first 20 clones sequenced, assuming a 350 bp read per clone. CviJ I cleavage at relaxed sites appears to be important in "filling gaps" left by normal restriction.

The primary goal of this effort was to determine the efficacy of these methods for rapid shotgun cloning and sequencing. For these purposes, only 100 bases of sequence data were acquired per clone. However, if 350 bases of sequence had been determined frown each clone, then the entire sequence of pUC19 would have been assembled from the overlap of the first 20 clones (FIG. 6). In this sequencing simulation 75% of pUC19 would have been sequenced at least 2 times from the first 20 clones. The highest degree of overfold sequencing would have been 6, and only involved 2.2% of the DNA. FIG. 6 also shows that most of the 1x sequencing coverage occurred in a region of the plasmid with a very low density of normal and relaxed CviJ I restriction sites. Most of the single coverage occurs in a 240 bp region of the plasmid between 1490 bp and 1730 bp where there are only 4 CviJ I relaxed sites. It should also be noted that by the 271 h randomly picked clone most of this region would have been covered a second time.

Figure 7:
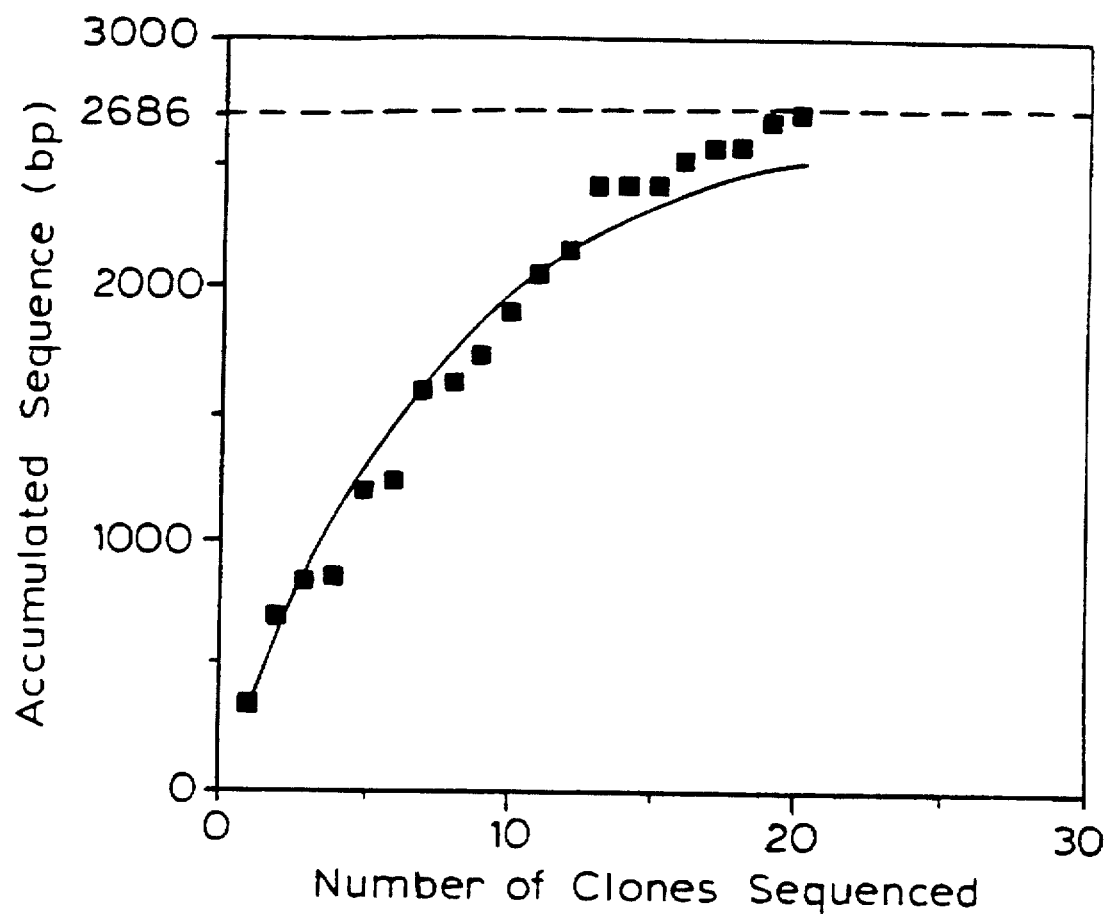
FIG. 7 is a graph of the rate of sequence accumulation by CviJ I** shotgun cloning and sequencing.

Shotgun sequencing strategies are efficient for accumulating the first 80–95% of the sequence data. However, the random nature of the method means that the rate at which new sequence is accumulated decreases as more clones are analyzed. In FIG. 7 the total amount of unique pUC19 sequence accumulated was plotted as a function of the number of clones sequenced. The points represent a plot of the total amount of determined pUC19 sequence versus the total number of clones sequenced. The horizontal dashed line demarcates the 2686 bp length of pUC19. The smooth curve represents a continuous plot of the discrete function $S(N)=NLe^{-cs}[((e^{cs}-1)/c)+(1-s)]$. The theoretical accumulation curve expected for a process in which sequence information is acquired in a totally random fashion is also shown. The smooth curve is a continuous plot of the discrete function $S(N)$ where $$S(N)=NLe^{-c\sigma}[((e^{c\sigma}-1)/c+(1-\sigma)].$$

This equation is based upon the results developed by Lander et al., *Genomics* 2:231–239 (1988) for the progress of contig generation in genetic mapping. In the equation: N is the number of clones sequenced, L is the length of clone insert in bp, c is the redundancy of coverage or LN/G (where G is length of fragment being sequenced in bp), and σ=1−θ, where θ is the fraction of length that two clones must share. The curve in FIG. 7 was calculated with G=2686 bp, L=350 bp, and σ=1. The plotted points lie close to the theoretical curve, and it thus appears that the sequence of pUC19 was accumulated in an apparent random fashion utilizing CviJ I** fragmentation and column fractionation.

EXAMPLE 9

Shotgun Cloning Utilizing 200 ng of Lambda DNA

Generally, 2–5 μg of DNA are needed for the sonication and agarose gel fractionation method of shotgun cloning in order to provide the several hundred colonies or plaques required for sequence analysis (Bankier et al. *Methods in Enzymol.* 155:51–93 (1987)). A ten-fold reduction in the amount of substrate required greatly simplifies the construction of such libraries, especially from large genomes, (Davidson, *J. DNA Sequencing and Mapping* 1:389–394 (1991)). The efficiency of constructing a large shotgun library from nanogram amounts of substrate was tested utilizing 200 ng of CviJ I**-digested lambda DNA. This material was column-fractionated as described previously. In this case, ½ of the column eluant (15 μl containing 50 ng of DNA) was ligated to 100 ng of Hinc II-digested and dephosphorylated pUC19 as described in Example 6. The cloning efficiencies of the control DNAs were similar to those reported in Tables 2 and 3. The 50 ng cloning experiment yielded 230 white colonies per ligation reaction in one trial, and 410 white colonies per ligation reaction in a second trial. Thus, it should be possible to routinely construct useful quasi-random shotgun libraries frown as little as 0.2–0.5 μg of starting material.

EXAMPLE 10

Epitope Mapping

CviJ I* recognizes the sequence GC (except for PyGCPu) in the target DNA. Under partial restriction conditions the length of fragment may be controlled by incubation time. Epitope mapping rising CviJ I** partial digests involves generating DNA fragments of 100–300 bp from a cDNA coding for the protein of interest, by methods described in Example 4, inserting them into an M13 expression vector, plating out on solid media, lifting plaques onto a membrane, screening for binding to the ligand of interest, and picking the positive plaques for isolation of the DNA, which is then sequenced to identify the epitope. Thus, the same epitope may be expressed as a small fragment or a larger fragment. This approach allows one to determine the smallest fragment containing the epitope of interest using functional assays such as binding to an antibody or other ligand, or using a direct assay for activity. For insertion into an M13 vector, linkers may be added to the fragments or the insert may be dephosphorylated to ensure that each fragment is cloned alone without ligation of multiple inserts.

The expression vectors recommended for subcloning of the CviJ I fragments are Lambda Zap™ (Stratagene, LaJolla, Calif.) or bacteriophage M13-epitope display vectors. An advantage of using an M13-based vector is that the peptide or protein of interest may be displayed along with the M13 coat protein and does not require host cell lysis in order to analyze the protein of interest. The lambda-based vectors yield plaques and hence the protein can be directly bound to a membrane filter.

EXAMPLE 11

Anonymous Primer Cloning

Primers are critical tools in many molecular biology applications such as PCR, sequencing, and as probes. Anonymous primers are useful as sequencing primers for genomic sequencing projects, as probes for mapping chromosomes, or to generate oligonucleotides for PCR amplification.

The Anonymous Primer Cloning (APC) method is a variation of shotgun cloning in that unknown sequences of DNA are being randomly cloned. However, unlike CviJ I shotgun cloning, wherein a partial CviJ I** digest of DNA is cloned, anonymous primer cloning utilizes a complete CviJ I* digest to restrict large DNAs into small fragments 20–200 bp in size. These small fragments are cloned into a unique vector designed for excising the anonymous DNA as labeled primers. The strategy for this method is illustrated in FIG. 8.

Figure 8B:
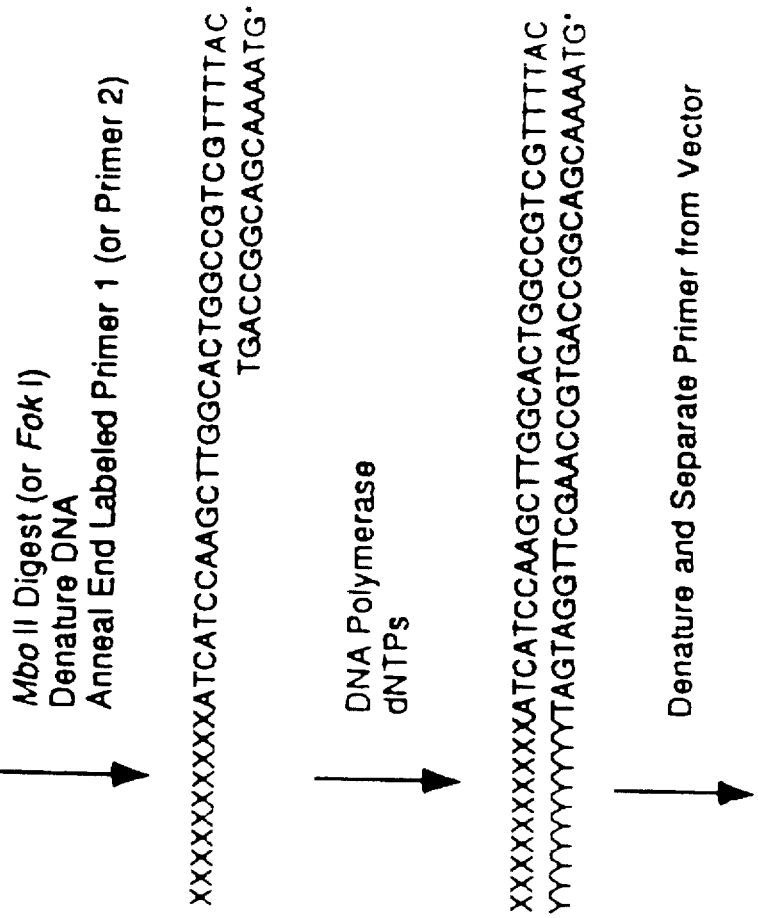

As illustrated in FIG. 8, the APC strategy reduces large DNAs to small fragments, which are cloned and excised for use as primers. Plasmid pFEM has a unique arrangement of the restriction sites for Mbo II and Fok I, which permits DNA cloned into the EcoR V site to be excised without associated vector DNA. This is possible because Fok I cleaves 9/13 bases to the left of the recognition site shown in pFEM and Mbo II cleaves 8/7 bases to the right of the recognition site shown in pFEM, which is well into the cloned anonymous sequence. After Mbo II or Fok I restriction, a known flanking primer is annealed (primer 1 or 2) and extended using a DNA polymerase and dNTPs. The palmer is previously end-labeled, or alternatively, one or more of the dNTPs is radioactive.

After denaturation of the newly synthesized DNA and separation from its cognate template, the labeled anonymous primer is ready for use in sequencing the original template from which it was subcloned. The presence of the pFEM vector sequence fused to the anonymous sequence does not influence the enzymatic extension of this primer from its unique binding site, as the vector DNA is at the 5' end and the unique sequence is located at the 3' end (all polymerases extend 5' to 3'). Both the top and bottom strand primers may be excised from pFEM due to the symmetrical placement of restriction sites and flanking primer binding sites. Thus, two primers may be derived from each cloning event. APC is particularly well suited to the genomic sequencing strategy of Church and Gilbert *Proc Natl. Acad Sci. U.S.A.* 81:1991–1995 (1984), although its utility is not limited thereto.

EXAMPLE 12

End Labeling of Restriction-Generated Oligonucleotides

As is clear from the foregoing examples, digesting DNA with CviJ I* provides the ability to generate sequence-specific oligonucleotides ranging in size frown 20–200 bases in length with an average length of 20–60 bases. Sequence specific oligonucleotides generated by CviJ I* digestion may be labeled directly at the 5'-end or at the 3'-end using techniques well known in that art.

For example, 5'-end labeling may be accomplished by either a forward reaction or an exchange reaction using the enzyme T4 polynucleotide kinase. In the forward reaction, $^{32}$P frown [$\gamma^{32}$P]ATP is added to a 5' end of an oligonucleotide which has been dephosphorylated with alkaline phosphatase using standard techniques widely known in the art and described in detail in Sambrook et al., *Molecular Cloning: A Laboratory Manual*, 2nd Edition. Cold Spring Harbor Laboratory Press (1989). In an exchange reaction, an excess of ADP (adenosine diphosphate) is used to drive an exchange of a 5'-terminal phosphate from the sequence specific oligonucleotide to ADP which is followed by the transfer of $^{32}$P from $\gamma^{32}$P-ATP to o the 5'-end of the oligonucleotide. This reaction is also catalyzed by T4 polynucleotide kinase and is described in Sambrook et al., *Molecular Cloning: A Laboratory Manual, 2nd Edition*. Cold Spring Harbor Laboratory Press (1989).

Homopolymeric tailing is another standard labeling technique useful in the labeling of CviJ I*-generated sequence specific oligonucleotides. This reaction involves the addition of $^{32}$P-labeled nucleotides to the 3'-end of the sequence specific oligonucleotides using a terminal deoxynucleotide transferase. (Sambrook et al., *Molecular Cloning: A Laboratory Manual, 2nd Edition*. Cold Spring Harbor Laboratory Press (1989)).

Commonly used labeling techniques typically employ a single oligonucleotide directed to a single site on the target DNA and containing one or a few labels. Oligonucleotides generated by the method of the present invention are directed to many sites of a target DNA by virtue of the fact that they are generated from a sample of the target sequence. Thus, the hybridization of multiple oligonucleotides (labeled by the methods described above) allows a significantly enhanced sensitivity in the detection of target sequences. In addition, the short length of the labeled oligonucleotides used in the methods of the present invention allows a reduction in hybridization time from overnight (as is used in conventional methods) to 60 mins.

Although labeling sequence specific oligonucleotides with $^{32}$P is described above, labeling with other radionucleotides, and non-radioactive labels is also within the scope of the present invention.

EXAMPLE 13

Primer Extension Labeling of DNA Using Restriction-Generated Oligonucleotides (PEL-RGO)

Another aspect of the present invention includes methods for labeling DNA which include the generation of oligonucleotide primers by complete digestion with CviJ I*, followed by heat denaturation. PEL-RGO requires three steps: 1) generating the sequence-specific oligonucleotides by CviJ I* restriction of the template DNA, 2) denaturation of the template and primer, and 3) primer extension in the presence of labeled nucleotide triphosphates. Plasmid DNA may be prepared by methods known in the art such as the alkaline lysis or rapid boiling methods (Sambrook et al., *Molecular Cloning: A Laboratory Manual, 2nd Edition*). Cold Spring Harbor Laboratory Press, Cold Spring Harbor, N.Y.(1989)). In addition, the vector should be linearized to ensure effective denaturation. A restriction fragment may be labeled after separation on low melting point agarose gels by methods well known in the art.

In PEL-RGO labeling, template DNA to be labeled is divided into two aliquots; one is used to generate the sequence specific oligonucleotide primers and the other aliquot is saved for the primer annealing and extension reaction. A typical reaction mix for generating sequence-specific oligonucleotides is assembled in a microcentrifuge tube and includes: 100 ng DNA; 2 μl 5x CviJ I* buffer; 0.5 μl CviJ I (1 u/μl); 10 μl sterile distilled water to final volume. CviJ I* 5X restriction buffer includes: 100 mM glycylglycine (Sigma, St. Louis, Mo., Cat. No. G2265) pH adjusted to 8.5 with KOH, 50 mM magnesium acetate (Amresco, Solon, Ohio, Cat. No. P0013119), 35 mM β-mercaptoethanol (Mallinckrodt, Pards, Ky., Cat. No. 60-24-2), 5 mM ATP, 100 mM dithiothreitol (Sigma, St. Louis, Mo., Cat. No. D9779) and 25% v/v DMSO, (Mallinckrodt Cat. No. 67-68-5). CviJ I is obtained from CHIMERx (Madison, Wis.) which is prepared as described in Example 3. The reaction mix is incubated at 37° C. for 30 min, followed by the inactivation of CviJ I by heating at 65° C. for 10 min. The CviJ I*-restricted DNA may be used directly without further purification, or it may be stored at −20° C. for several months for subsequent labeling reactions.

After heat-inactivating CviJ I, 0.2 μg of the digested and undigested DNA are electrophoresed on a 1.5% agarose gel, using a suitable molecular weight marker for comparison. The CviJ I restriction fragments appear as a low molecular weight smear in the 20–200 bp range.

By way of example, 1–10 ng of linearized pUC19 was labeled under the conditions described below. A template-primer cocktail was prepared by mixing 10 ng of linearized pUC19 DNA template with 20 ng pUC19 sequence-specific oligonucleotides (prepared as described above) and the mixture is brought to a final volume of 17 μl with sterile distilled water. The template-primer mixture is denatured in a boiling water bath for 2 minutes and immediately placed on ice.

The following labeling mixture is then added to the template-primer mix:2.5 μl 10X labeling buffer (500 mM Tris HCl at pH 9.0, 30 mM MgCl$_2$, 200 mM (NH$_4$)$_2$SO$_4$, 20 μM dATP, 20 μM dTTP, 20 μM dGTP, 0.4% NP-40); 5.0 μl [α-$^{32}$P] dCTP (3000Ci/mmol, 10 μCi/μl New England Nuclear, Catalog No. NEG013H); 0.5 μl *Thermus flavus* DNA polymerase (5 u/μl) (Molecular Biology Resources, Milwaukee, Wis.); up to 25 μl final volume with distilled water. The reaction was incubated at 70° C. for 30 min and then stopped by adding 2 μl of 0.5M EDTA at pH 8.0 to the reaction mix.

The efficiency of the labeling reaction is gauged by the percentage of radioisotope incorporated into labeled DNA. One microliter of the labeling reaction is added to 99 μl of 10 mM EDTA in a microcentrifuge tube. This serves as the source of diluted probe for total and trichloroacetic acid (TCA)-precipitable counts. 2 μl of diluted probe is spotted onto the center of a glass fiber filter disc (Whatman number 934-AH). The disc is then allowed to dry and is then placed in a vial containing scintillation cocktail for counting total radioactivity in a liquid scintillation counter. Another 2 μl aliquot from the diluted probe is added to 1 ml of 10% ice cold TCA followed by the addition of 2 μl of carrier bovine serum albumin (BSA). This mixture was then placed on ice for 10 minutes. The precipitate is then collected on a glass filter disc (Whatman No. 934-AH) by vacuum filtration. The filter is then washed with 20 ml of ice cold 10% TCA, allowed to dry and is placed in a vial containing scintillation cocktail and counted.

Because primer extension oligonucleotide labeling results in net DNA synthesis, the specific activity of labeled DNA is calculated using the following guidelines.

Total cpm incorporated=TCA cpm×50×27

Wherein the factor 50 is derived from using 2 μl of a 1:100 dilution for TCA precipitation. The number 27 converts this back to the total reaction volume (which is the reaction volume plus 2 μl of stop solution).

Synthesized DNA (ng of DNA synthesized) = theoretical yield X fraction of radioactivity incorporated.

Theoretical yield (ng of DNA) =

$$\frac{\mu Ci\ dNTPs\ added \times 4 \times 330\ ng/nmole}{specific\ activity\ dNTP(Ci/nmole = \mu Ci/nmole)}$$

Fraction of incorporated label = TCA precipitated cpm/total cpm.

$$\frac{Specific\ activity}{(cpm/\mu g\ of\ DNA)} = \frac{total\ cpm\ incorporated \times 1000}{synthesized\ DNA + input\ DNA}$$

Wherein 1000 is the factor converting nanograms to micrograms.

By way of example, the following represents the calculation of specific activity for an aliquot of pUC19 DNA labeled using this method. Using 50 μCi of [α-$^{32}$P]dCTP in a 25 μl reaction, and if the TCA precipitated cpm is 26192 and total cpm is 102047;

Total cpm incorporated = $26192 \times 50 \times 27 = 3.27 \times 10^7$ cpm

Synthesized DNA (ng of DNA synthesized) =

Theoretical yield X fraction of radioactivity incorporated.

$$Theroretical\ yield = \frac{\mu Ci\ of\ dNTPs \times 4 \times 330}{3000\ \mu Ci/nmole}$$

$$= \frac{50\ \mu Ci \times 4 \times 330}{3000}$$

$$= 22\ ng$$

$$\frac{Fraction\ of}{label\ incorporated} = \frac{TCA\ precipitated\ cpm}{Total\ cpm} = \frac{26192}{102047} = 0.256$$

Synthesized DNA = $22 \times 0.256$
= 5.6 ng $$\frac{Specific\ activity}{(cpm/\mu g)} = \frac{Total\ cpm\ incorporated}{Synthesized\ DNA + input\ DNA} \times 1000$$

Input DNA = 10 ng

Specific activity = $\frac{3.27 \times 10^7}{5.6 + 10} \times 1000$

= $2.09 \times 10^9$ cpm/μg

Unincorporated radioactive label may be removed using standard methods well known in the art.

Comparisons were undertaken between PEL-RGO vs RPL under similar conditions, and it was observed that a detection limit of 100 fg was seen using PEL-RGO labeled DNA compared to a detection limit of 500 fg with RPL, using a radiolabeled probe.

EXAMPLE 14

Thermal Cycle Labeling

Thermal Cycle Labeling (TCL) is a method according to the present invention for efficiently labeling double-stranded DNA while simultaneously amplifying large amounts of the labeled probe. TCL of DNA requires two general steps: 1) generation of the sequence-specific oligonucleotides by CviJ I*-restriction of the template DNA, and 2) repeated cycles of denaturation, annealing, and extension in the presence of a thermostable DNA polymerase. Optimal results are obtained after 20 such cycles, which is best performed in an automated thermal cycling instrument such as a Perkin-Elmer Model 480 thermocycler. In conjunction with such an instrument, about 2.5 hr are required to complete this protocol. If a thermal cycler is not available these reactions may be performed using heat blocks. As few as 5 cycles may yield probes with acceptable detection sensitivities.

Non-radioactive labeling of DNA using TCL is accomplished by mixing: 10 ng linearized template, 50 ng CviJ I*-digested primers (prepared as described above), 1.5 μl 10X labeling buffer, 0.5 μl *Thermus flavus* DNA polymerase (5 u/μl) (Molecular Biology Resources, Inc., Milwaukee, Wis.), 1 μl of 1 mM Biotin-11-dUTP (Enzo Diagnostics, New York, N.Y.), 1.5 μl each of dATP, dCTP, and dGTP (2 mM), and 1.0 μl 2 mM dTTP.

Radioactive labeling of DNA using TCL was accomplished by mixing 10–20 ng of CviJ I primers, 10 pg-25 ng of linearized template, 1.5 μl of 10X labeling buffer, 2.5 μl of $^{32}$P-dCTP (3000 Ci/mmole, 10 μCi/μl or 40 μCi/μl), 0.5 μl of *Thermus flavus* DNA polymerase (5u/μl), and 0.5 μl each of dATP, dGTP, and dTTP (1 mM) was added. The reaction mix was brought to a volume of 15 μl with deionized H$_2$O, overlaid with mineral oil and cycled through 20 rounds of denaturation, annealing and extension. A typical cycling regimen employed 20 cycles of denaturation at 91° C. for 30 sec, annealing at 50° C. for 30 sec and extension at 72° C. for 2 min. The reaction is then terminated by adding 1 μl of 0.5M EDTA, pH 8.0. The amplified, labeled probe is a very heterogeneous mixture of fragments, which appears as a large molecular weight smear when analyzed by agarose gel electrophoresis.

Estimation of Bio-11 dUTP incorporation:

In order to estimate the level of incorporation of biotin-11-dUTP into DNA, a serial dilution from 1:10 to 1:108 of the labeled probe (free of unincorporated biotin-11-dUTP) is made in TE (10 mM Tris, 1 mM EDTA, pH 8). A microliter of each dilution is placed on a neutral nylon membrane, and the DNA sample is bound to the membrane either by UV cross linking for 3 min or by baking at 80° C. for 2 hr.

The unbound sites on the membrane are blocked using a blocking buffer for 30–60 min at 25° C. Streptavidin-alkaline phosphatase (Gibco-BRL Gaithersburg, Md., Cat. No. 9545A) is added to the blocking buffer (0.058M Na$_2$HPO$_4$, 0.017M NaH$_2$PO$_4$, 0.068M NaCl, 0.02% sodium azide, 0.5% casein hydrolysate, 0.1% Tween-20) at a 1:5000 dilution and incubated for an hour, and the membrane is rinsed 3 times with wash buffer (1x PBS [0.058M Na$_2$HPO$_4$, 0.017M NaH$_2$PO$_4$, 0.068M NaCl], 0.3% Tween, 0.2% sodium azide), rinsed briefly (5 minutes) with AP buffer (100 mM NaCl 5 mM MgCl$_2$, 100 mM Tris-Cl pH 9.5) and then enough AP buffer containing 4.0 μl/ml nitro blue tetrazolium (NBT) (Sigma Cat. No. N6639), (Sigma Cat. No. B6777), and 3.5 μl/ml of 5-bromo-4-chloro-3-indolyl phosphate (BCIP) was added in order to cover the membrane. The membrane is left in the dark for approximately 30 minutes or until the reaction is complete. The reaction is stopped by rinsing in 1 X PBS.

Detection Sensitivities $^{32}$P-labeled probes generated by the TCL protocol detect as little as 50 zeptomoles ($2.5 \times 10^{-20}$ moles) of a target sequence. As little as 10 pg of template DNA is enough to synthesize 5–10 ng of radiolabeled probe, which is sufficient for screening 5 Southern blots. This radioactive version of TCL facilitates extremely high specific activities of labeled probe (1–2×10$^{10}$ cpm/μg DNA), which permits 5–10 fold lower detection limits than conventional labeling protocols. The synthesis of higher specific activity probes is probably the net result of the sequence- specific oligonucleotide primers and their increased length when compared to the short random primers used in other labeling methods. In addition, the thermal cycling permits probe amplification.

Biotin-labeled probes generated by the TCL protocol detect as little as 25 zeptomoles (2.5×10$^{-20}$ moles) of a target sequence. A 50 μl TCL reaction yields as much as 25 μg of labeled DNA, enough to probe 25 to 50 Southern blots. Biotin-labeled TCL probes provide a 10 fold greater detection sensitivity compared to RPL biotin probes. In addition, the thermal cycling permits probe amplification.

Non-radioactive, biotinylated probes labeled by the TCL method were shown to have detection limits that are identical to the radioactive probes. This method has an advantage of eliminating the need to work with hazardous radioactive materials without sacrificing sensitivity. In addition, results are obtained from non-isotopic probes in 3–4 hours compared to 3–4 days for radiolabeled probes. The ability to substitute non-radioactive probes for radioactive probes may be very useful to clinical laboratories, which do not use radioisotopes but do need greater detection sensitivities. Research laboratories favor the use of non-isotopic systems if detection sensitivity is not an issue. The non-isotopic labeling version of the TCL system represents a major improvement in labeling DNA probes. Non-radioactive probes generated by the methods of the present invention are also useful in the detection of RNA in situ. An advantage of this system is that TCL labeling yields highly sensitive, non-radioactive probes, and the size of the probes are predominantly in the small molecular weight range and can therefor penetrate the tissue easily, unlike RPL. Because non-radioactive probes labeled using TCL labeling have the same detection limits as do radioactive probes similarly labeled, it is within the scope of this invention to use either radioactive or non-radioactive probes for probing, for example, Southern blots, Northern blots, and for in situ hybridization for the detection of mRNA in cells or tissue directly.

TCL has also been accomplished using sequence-specific oligonucleotides generated by CGase I digestion described below.

EXAMPLE 15

CGase I

CGase I as used herein, refers to a restriction endonuclease reagent which cleaves DNA at the dinucleotide CG. CGase I activity is based on the combined star activities of the restriction endonucleases Hpa II and Taq I. Under normal reaction conditions (10 mM Bis Tris Propane-HCl pH 7.0, 10 mM MgCl$_2$, 1 mM DTT; 1 unit of enzyme/μg DNA, 37° C. for 1 hr), Hpa II recognizes CCGG and cleaves after the first C to leave a 2-base 5' overhang. Under normal reaction conditions (100 mM NaCl, 10 mM Tris-HCl pH 8.4, 10 mM MgCl$_2$, 10 mM 2-mercaptoethanol, 1 unit of enzyme/μg DNA, 65° C. for 1 hr) the restriction endonuclease Taq I recognizes TCGA and cleaves after the T to leave a 2-base 5' overhang.

Reaction conditions have been described for Taq I* activity which decrease the cleavage specificity of Taq I (10 mM Tris-HCl pH 9.0, 5 mM MgCl$_2$, 6 mM 2-mercaptoethanol, 20% DMSO; 2000 units of enzyme/μg DNA, 65° C. for 1 hr) (Barany, Gene, 65:149–165 (1988)). These reaction conditions allow Taq I* to cleave DNA at the following sequences:

| Taq I* | TCGA |
|---|---|
| | CCGA (TCGG) |
| | ACGA (TCGT) |
| | TCTA (TAGA) |
| | TCAA (TTGA) |
| | GCGA (TCGC) |

We are unaware of any literature descriptions of Hpa II* conditions. However, the following conditions were established to promote Hpa II* activity which are also compatible with Taq I* activity: 5 mM KCl, 10 mM Tris-HCl pH 8.5, 10 mM MgCl$_2$, 1 mM DTT, 15% DMSO, 100 ug/ml BSA (CGase buffer); 50 units of enzyme/μg DNA 50° C. for 1 hr. The Hpa II* recognition sites were determined by cloning and sequencing Hpa II* restricted fragments. The characterized Hpa II* recognition sequences are as follows:

| Hpa II* | CCGG |
|---|---|
| | CCGC (GCGG) |
| | CCGA (TCGG) |
| | ACGG (CCGT) |

Taq I (400 units/μg DNA) and Hpa II (50 units//μg DNA) were then combined (CGase I) in CGase I buffer and the following recognition sites were identified by cloning and sequencing restricted pUC19 fragments.

| CGase I | GCGC |
|---|---|
| | TCGA |
| | CCGG |
| | GCGT |
| | ACGA |
| | ACGG (CCGT) |
| | GCGG (CCGC) |
| | CCGA (TCGG) |

CGase I restriction of natural DNA, (i.e. pUC19, lambda), results in fragments ranging from 20–200 bp in length (average 20–60 bp). Heat denaturation of these fragments generates numerous oligonucleotides of variable length but precise specificity for the cognate template as was the case with CviJ I* digestion. CGase I restriction of the small plasmid pUC19 (2689 bp) theoretically yields 174 restriction fragments, or 384 oligonucleotides after a heat denaturation step.

The "two-cutter" activity of CviJ I* and CGase I represent a unique class of restriction endonuclease activity in that no other known restriction endonucleases will generate this size range of oligonucleotides. The ability to generate numerous oligonucleotides with perfect sequence specificity from any DNA, without regard to sequence composition, genetic origin, or prior sequence knowledge is one of the properties that CGase I shares with CviJ I*. In addition, the generation of numerous oligonucleotides by CviJ I or CGase I results in a form of probe or primer amplification not practical using conventional means of organic synthesis.

Based on ability to recognize a dinucleotide sequence, the present invention contemplates the interchangeability of CGase I with CviJ I* in all of the applications described herein.

Although the present invention has been described in types of preferred embodiments, it is intended that the present invention encompass all modifications and varia-

We claim:

1. A method for labeling DNA, the method comprising the steps a) digesting an aliquot of template DNA with a restriction endonuclease reagent that is CviJ I or Taq I and Hpa II in combination, under conditions that generate sequence-specific DNA fragments from about 20 to about 200 base pairs in length and having an average length of about 20 to about 60 base pairs;

b) mixing an aliquot of undigested template DNA with said sequence-specific DNA fragments, denaturing said mixture of template DNA and sequence-specific DNA fragments thereby generating denatured template DNA and oligonucleotide primers;

c) annealing said primers to said denatured undigested template DNA to form a DNA-primer complex;

d) performing an extension reaction from said primers in said DNA-primer complex using a DNA polymerase in the presence of one or more nucleotide triphosphates that comprise at least one labeled nucleotide triphosphate.

2. The method according to claim 1 wherein said restriction endonuclease reagent comprises CviJ I.

3. The method according to claim 1 wherein said restriction endonuclease reagent comprises in combination, Taq I and Hpa II.

4. The method according to claim 1 wherein said extension reaction is performed by a DNA polymerase.

5. The method according to claim 4 wherein said DNA polymerase is *Thermus flavus* DNA polymerase.

6. The method according to claim 1 wherein the one or more nucleotide triphosphates are selected from the group consisting of dATP, dCTP, dGTP, dUTP and dTTP.

7. The method according to claim 1 wherein said label is selected from the group consisting of $^{32}P$, $^{33}P$, $^{3}H$, $^{14}C$, and $^{35}S$.

8. The method according to claim 1 wherein said labeled nucleotide triphosphate is selected from the group consisting of biotin-labeled nucleotide triphosphates, fluorescein-labeled nucleotide triphosphates, dinitrophenol-labeled nucleotide triphosphates, and digoxigenin-labeled nucleotide triphosphates.

9. A kit for labeling DNA, said kit comprising in association:

a) a restriction endonuclease reagent comprising CviJ I or Taq I and Hpa II in combination;

b) a restriction endonuclease buffer that when combined with said restriction endonuclease reagent causes said restriction endonuclease reagent to digest an aliquot of template DNA to produce sequence-specific DNA fragments from about 20 to about 200 base pairs in length and having an average length of about 20 to about 60 base pairs; and c) a labeling buffer.

10. The kit according to claim 9 wherein said restriction endonuclease reagent comprises CviJ I.

11. The kit according to claim 10 wherein said restriction endonuclease buffer is CviJ I* restriction endonuclease buffer.

12. The kit according to claim 9 wherein said restriction endonuclease reagent comprises in combination, Taq I and Hpa II.

13. The kit according to claim 12 wherein said restriction endonuclease buffer is CGase I buffer.

14. The kit of claim 9 further comprising:

d) a concentrated mixture of one or more nucleotide triphosphates; and e) a DNA polymerase.

15. The kit according to claim 14 wherein said nucleotide mixture is an equimolar mixture of one or more nucleotides selected from the group consisting of dCTP, dTTP, dATP, and dGTP.

16. The kit according to claim 14 additionally comprising a labeled nucleotide selected from the group consisting of biotin-11-dUTP, digoxigenin-11-dUTP and fluorescein-11-dUTP.

17. The kit according to claim 14 additionally comprising a labeled nucleotide selected from the group consisting of $^{32}$P-labeled nucleotides, $^{33}$P-labeled nucleotides, $^{14}$C-labeled nucleotides, $^{35}$S-labeled nucleotides, and $^{3}$H-labeled nucleotides.

18. The kit according to claim 14 wherein said DNA polymerase is the Klenow fragment of DNA polymerase 1.

19. The kit according to claim 14 wherein said DNA polymerase is a thermostable DNA polymerase.

20. The kit according to claim 19 wherein said thermostable DNA polymerase is *Thermus flavus* DNA polymerase.

21. A method for thermal-cycle labeling DNA comprising the steps of:

a) digesting an aliquot of template DNA with a restriction endonuclease reagent under conditions wherein said template DNA is cleaved at one or more nucleotide sequences selected from the group consisting of PyGCPy, PuGCPy, PuGCPu, and PyCGPu and wherein Pu=purine and Py=pyrimidine, thereby generating sequence specific DNA fragments;

b) mixing an aliquot of undigested template DNA with an excess of said sequence specific DNA fragments, denaturing said mixture of template DNA and said excess of sequence specific DNA fragments, thereby generating denatured template DNA and excess oligonucleotide primers;

c) annealing said primers to said undigested template DNA to form a DNA-primer complex;

d) performing an extension reaction from said primers in said DNA-primer complex using a DNA polymerase in the presence of one or more nucleotide triphosphates that comprise at least one labeled nucleotide triphosphate, thereby producing labeled extension products;

e) heat-denaturing said labeled extension products from said template DNA;

f) reannealing said excess primers with said template DNA and with said extension products; and g) performing at least one additional extension reaction using a DNA polymerase.

22. The method according to claim 21 wherein said label is selected from the group consisting of $^{32}$P, $^{33}$P, $^{3}$H, $^{14}$C, and $^{35}$S.

23. The method according to claim 21 wherein said label is selected from the group consisting of fluorescein, dinitrophenol, biotin, and digoxigenin.

24. The method according to claim 21 wherein said DNA polymerase is a heat stable DNA polymerase.

25. The method according to claim 24 wherein said heat-stable DNA polymerase is *Thermus flavus* DNA polymerase or a functional fragment thereof and wherein said fragment maintains polymerase activity.

26. The method according to claim 21, wherein said one or more nucleotide triphosphates are selected from the group consisting of dATP, dCTP, dGTP, dTTP and at least one labeled nucleotide triphosphate.

27. The method according to claim 21 wherein said restriction endonuclease reagent is selected from the group consisting of CGase I and CviJ I*.

28. The method of claim 21 wherein said digestion generates DNA fragments from 18 base pairs in length to 200 base pairs in length and wherein said fragments have an average length of 20 to 60 nucleotides.

29. The method according to claim 21 wherein steps e)–g) are repeated up to 20 times.

\* \* \* \* \*

UNITED STATES PATENT AND TRADEMARK OFFICE
CERTIFICATE OF CORRECTION

PATENT NO.   : 5,604,098
DATED        : February 18, 1997
INVENTOR(S)  : Mead et al.

It is certified that error appears in the above-identified patent and that said Letters Patent is hereby corrected as shown below:

Column 1,
Line 46, replace "H" with -- II --

Column 2,
Line 56, replace "at." with "al."

Column 4,
Line 7, replace "355-337" with -- 335-337" (As per Amendment dated 02/06/96, page 1)

Column 5,
Line 35, replace "at." with -- al. --

Column 10,
Line 58, replace "frown" with -- from --

Column 11,
Line 24, replace "endonncleases" with -- endonucleases --

Column 16,
Line 32, replace "K/PO4" with -- $K/PO_4$ --

Column 17,
Line 1, replace "frown" with -- from --

Column 21,
Line 7, replace "frown" with -- from --
Line 35, replace "CvJI" with -- CviJI --

Column 26,
Line 33, replace "frown" with -- from --
Line 45, replace "271h" with -- 27th --

Column 28,
Line 36, replace "palmer" with -- primer --
Line 63, replace "frown" with -- from --

Column 29,
Line 13, after "to" and before "the" (1st occurrence) delete [o]

UNITED STATES PATENT AND TRADEMARK OFFICE
CERTIFICATE OF CORRECTION

PATENT NO. : 5,604,098
DATED : February 18, 1997
INVENTOR(S) : Mead et al.

It is certified that error appears in the above-identified patent and that said Letters Patent is hereby corrected as shown below:

Column 33,
Line 36, replace "therefor" with -- therefore --

Signed and Sealed this

Twenty-sixth Day of February, 2002

Attest:

Attesting Officer

JAMES E. ROGAN
Director of the United States Patent and Trademark Office